(12) United States Patent
Bang et al.

(10) Patent No.: US 10,036,007 B2
(45) Date of Patent: Jul. 31, 2018

(54) METHOD OF SYNTHESIS OF GENE LIBRARY USING CODON RANDOMIZATION AND MUTAGENESIS

(71) Applicant: CELEMICS, INC., Seoul (KR)

(72) Inventors: Duhee Bang, Seoul (KR); Sangun Park, Seoul (KR); Joongoo Lee, Pocheon-si (KR); Jeewon Lee, Seoul (KR)

(73) Assignee: CELEMICS, INC., Seoul (KR)

( * ) Notice: Subject to any disclaimer, the term of this patent is extended or adjusted under 35 U.S.C. 154(b) by 314 days.

(21) Appl. No.: 14/650,871

(22) PCT Filed: Dec. 11, 2013

(86) PCT No.: PCT/KR2013/011492
§ 371 (c)(1),
(2) Date: Jun. 10, 2015

(87) PCT Pub. No.: WO2014/092458
PCT Pub. Date: Jun. 19, 2014

(65) Prior Publication Data
US 2015/0329854 A1   Nov. 19, 2015

(30) Foreign Application Priority Data
Dec. 11, 2012 (KR) .......... 10-2012-0143980

(51) Int. Cl.
*C12N 15/10* (2006.01)
*C12N 15/67* (2006.01)

(52) U.S. Cl.
CPC ....... *C12N 15/102* (2013.01); *C12N 15/1093* (2013.01); *C12N 15/67* (2013.01)

(58) Field of Classification Search
CPC ... C12N 15/102; C12N 15/1093; C12N 15/67
(Continued)

(56) References Cited

U.S. PATENT DOCUMENTS 4,683,202 A * 7/1987 Mullis .................. B01L 7/52
                                              435/317.1
7,058,515 B1   6/2006 Selifonov et al.
(Continued)

FOREIGN PATENT DOCUMENTS

CN      1836041 A    9/2006
CN    101313078 A   11/2008
(Continued)

OTHER PUBLICATIONS

International Search Report for PCT/KR2013/011492 dated Apr. 3, 2014 from Korean Intellectual Property Office.
(Continued)

*Primary Examiner* — Karla A Dines
(74) *Attorney, Agent, or Firm* — STIP Law Group, LLC

(57) ABSTRACT

Proposed is a method of easily finding an error during analysis of various library sequences of nucleic acid base sequences after synthesizing a gene library using a combination of three nucleic acid base sequences (codon) translated into the same protein. This shows that it is possible to create a gene library having the same protein sequence but different nucleic acid base sequences. The present disclosure provides a novel experimental method capable of measuring a correlation between gene expression according to change in a codon by changing the usage of a codon optimized to express a specific gene in vivo.

14 Claims, 23 Drawing Sheets

(58) Field of Classification Search
USPC .......................................................... 506/16
See application file for complete search history.

(56) References Cited

U.S. PATENT DOCUMENTS

| | | |
|---|---|---|
| 2002/0183934 A1 | 12/2002 | Selifonov et al. |
| 2004/0214295 A1* | 10/2004 | Fujii ..................... C12N 9/00 435/110 |
| 2005/0136428 A1 | 6/2005 | Crea |
| 2009/0234101 A1* | 9/2009 | Ladner .................. C40B 40/02 530/350 |
| 2012/0015820 A1 | 1/2012 | Patten et al. |
| 2012/0309633 A1 | 12/2012 | Van Eijk et al. |
| 2014/0080716 A1 | 3/2014 | Van Eijk et al. |
| 2014/0309118 A1 | 10/2014 | Bang et al. |

FOREIGN PATENT DOCUMENTS

| | | |
|---|---|---|
| EP | 1130093 A1 | 9/2001 |
| EP | 2202308 A2 | 6/2010 |
| JP | 2002537758 A | 11/2002 |
| KR | 10-2001-0085850 A | 9/2001 |
| KR | 10-2006-0034650 A | 4/2006 |
| WO | 9827230 A1 | 6/1998 |

OTHER PUBLICATIONS

Duhee Bang, Hwangbeom Kim, Hyojun Han, 2011, 10-2011-0076408, "Shot gun DNA Synthesis for the High-throughput Construction of Large DNA Molecules".

Mol Biosyst. Jul. 2009;5(7):714-22.doi: 10.1039/b822268c. Epub Apr. 6, 2009.

Carr,P.A. and Church,G.M. (2009) Genome engineering. Nat. Biotechnol., 27, 1151-1162.

Patwardhan RP, Lee C, Litvin O, Young DL, Pe'er D, Shendure J. Nature Biotechnology, 27, 1173-1175.(2009).

Whitehead TA, Chevalier A, Song Y, Dreyfus C, Fleishman SJ, De Mattos C, Myers CA, Kamisetty H, Blair P, Wilson IA, Baker D. Nature Biotechnology, 30, 543-548.(2012).

DeKosky BJ, Ippolito GC, Deschner RP, Lavinder JJ, Wine Y, Rawlings BM, Varadarajan N, Giesecke C, Dorner T, Andrews SF, Wilson PC, Hunicke-Smith SP, Willson CG, Ellington AD, Georgiou G. Nature Biotechnology, 31, 166-169.(2013).

Larman HB, Xu GJ, Pavlova NN, Elledge SJ. PNAS, 109, 18523-18528.(2012).

Willem P. C. Stemmer, "DNA shuffling by random fragmentation and reassembly: In vitro recombination for molecular evolution", Proc. Natl. Acad. Sci. USA, Oct. 1994, pp. 10747-10751, vol. 99.

Cameron Neylon, "Chemical and biochemical strategies for the randomization of protein encoding DNA sequences: library construction methods for directed evolution", Nucleic Acids Research, 2004, pp. 1448-1459, vol. 32, No. 4.

Masayuki Endo, et al., "Programmed-Assembly System Using DNA Jigsaw Pieces", Chemistry—A European Journal, 2010, pp. 5362-5368, vol. 16.

Extended European Search Report of EP13863345.8 dated Apr. 4, 2016.

Cho, Namjin et al., De novo assembly and next-generation sequencing to analyse full-length gene variants from codon-barcoded libraries, Nature Communications, Sep. 21, 2015, pp. 1-36, DOI: 10.1038/ncomms9351.

* cited by examiner

[Fig. 1]
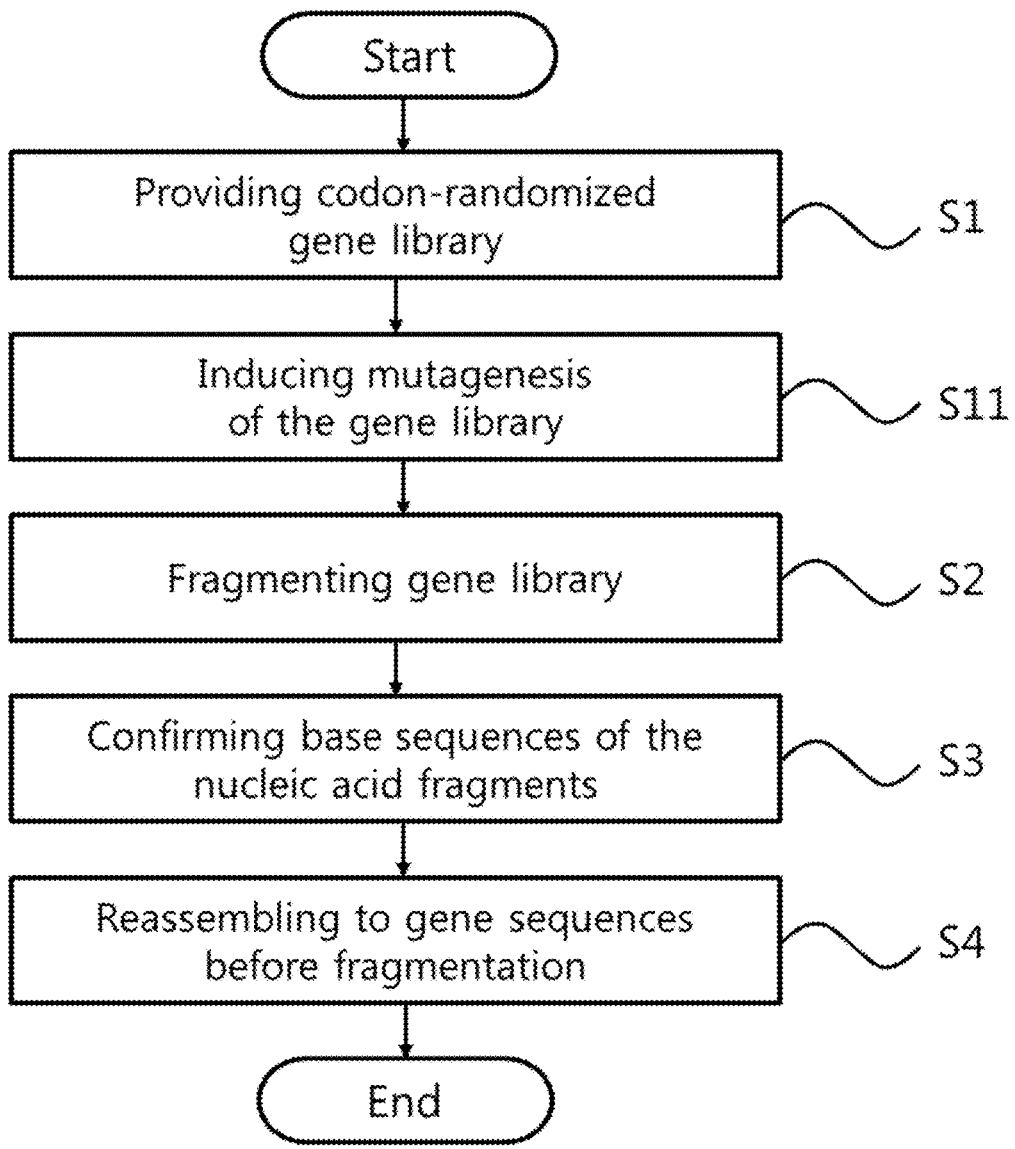

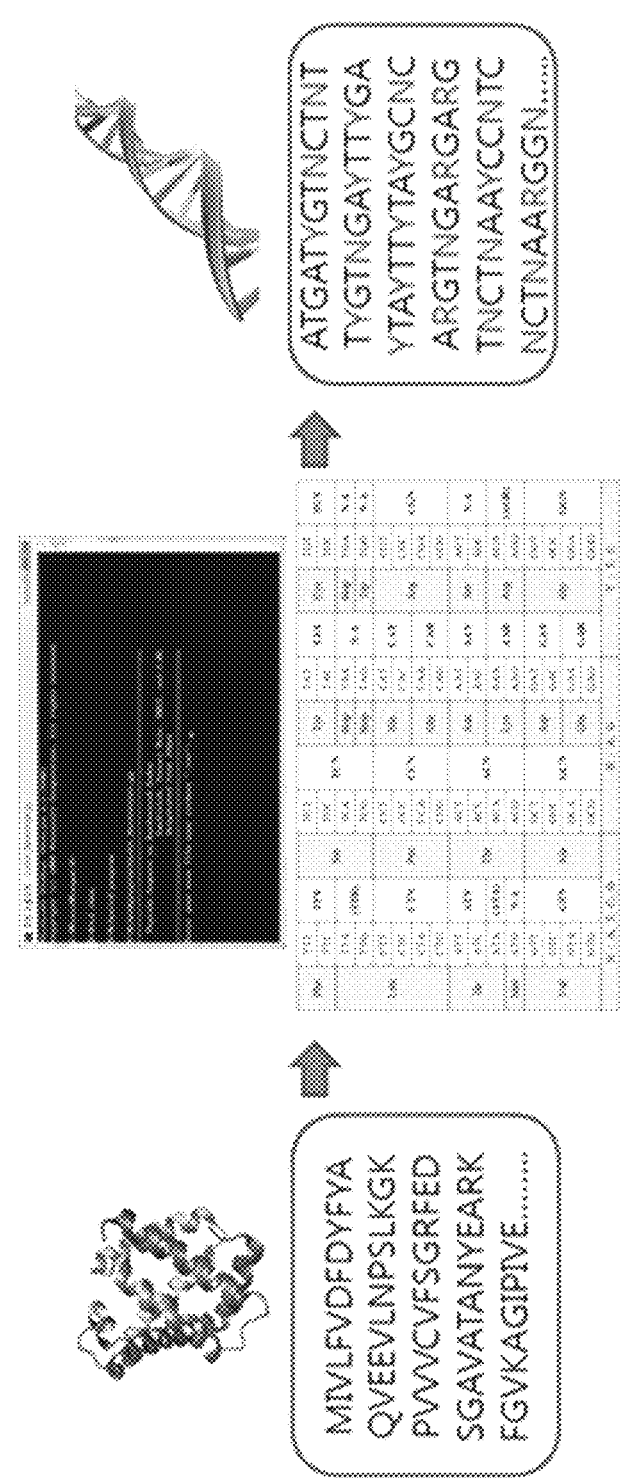

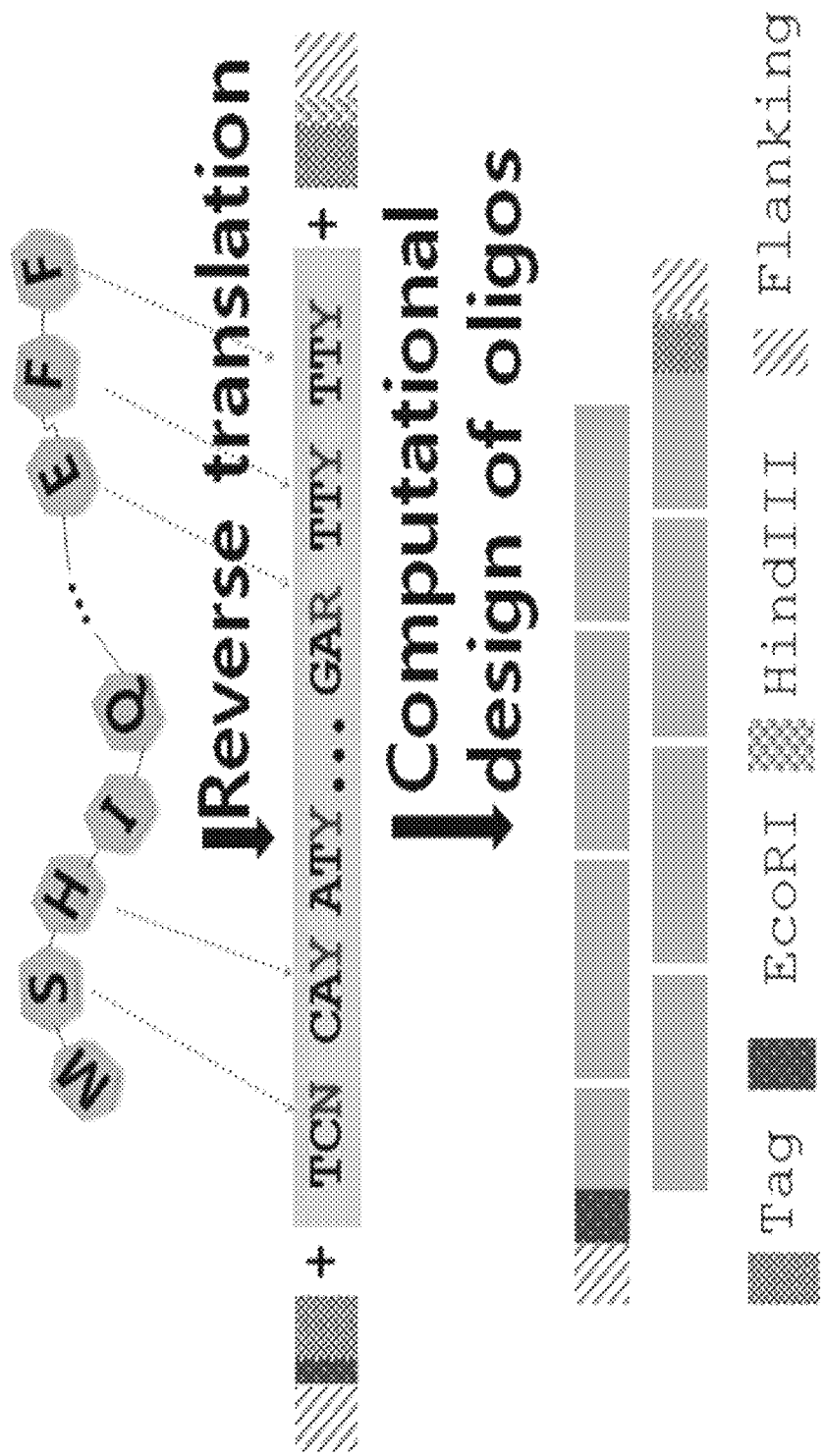
[Fig. 3]

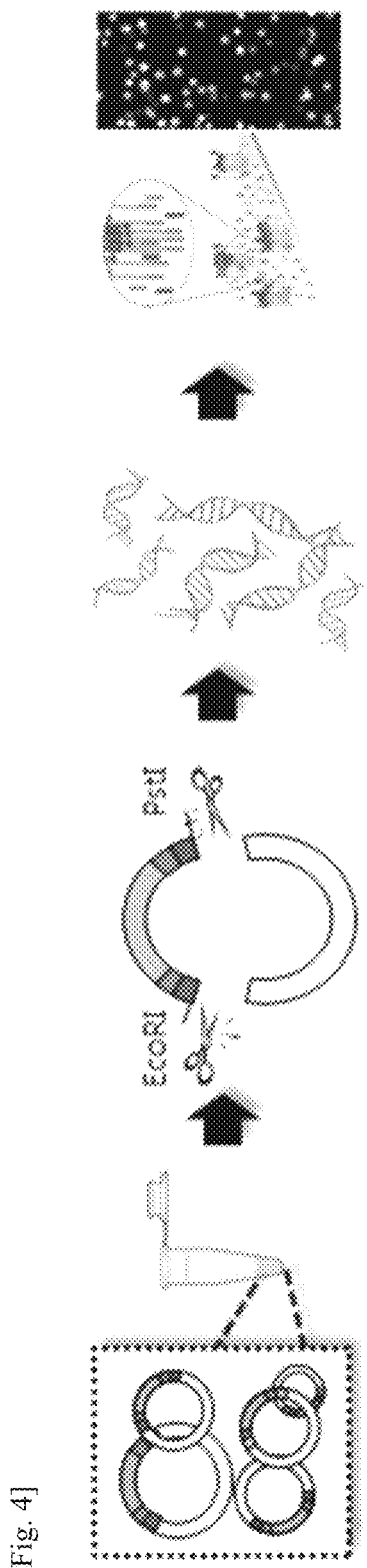
[Fig. 4]

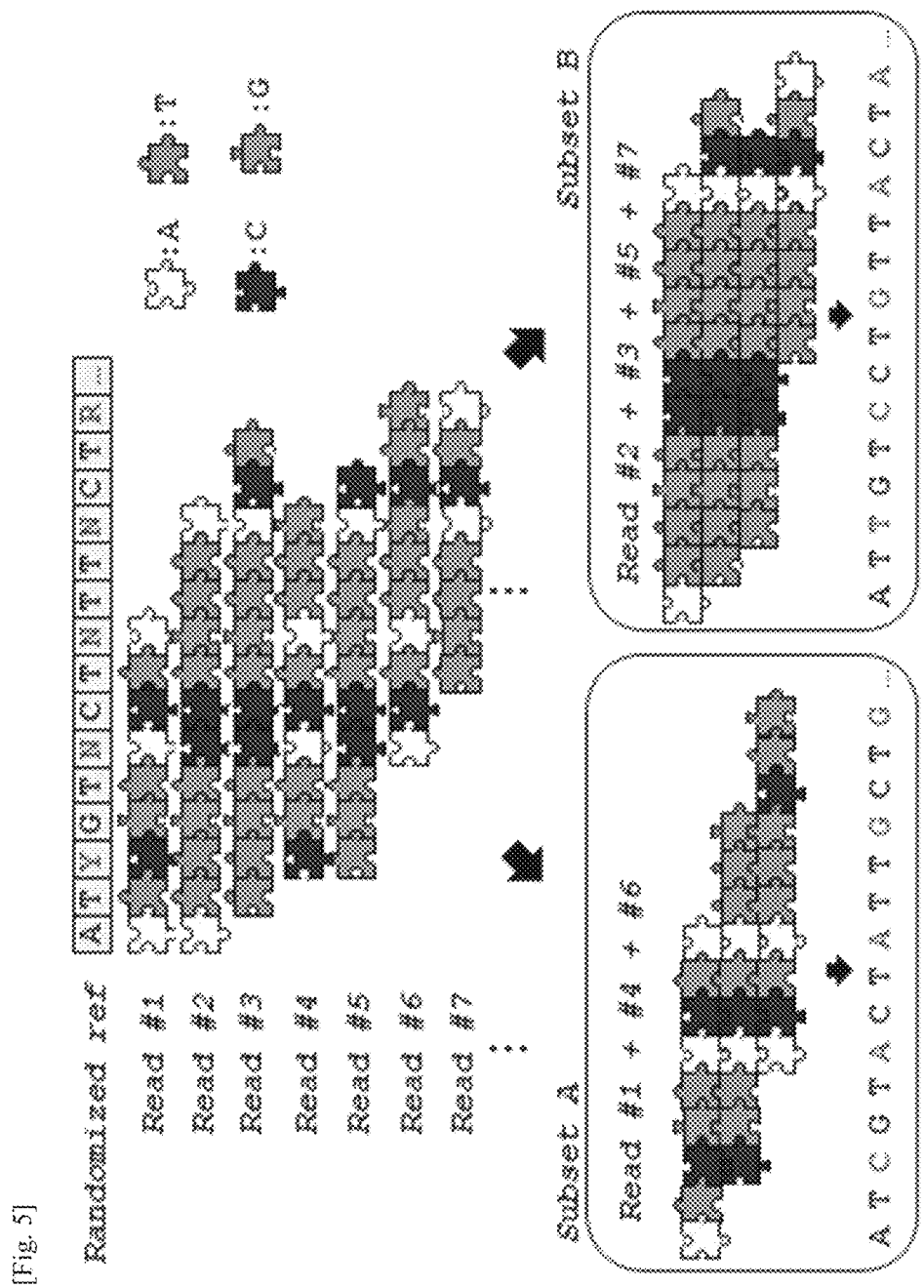
[Fig. 5]

[Fig. 6]
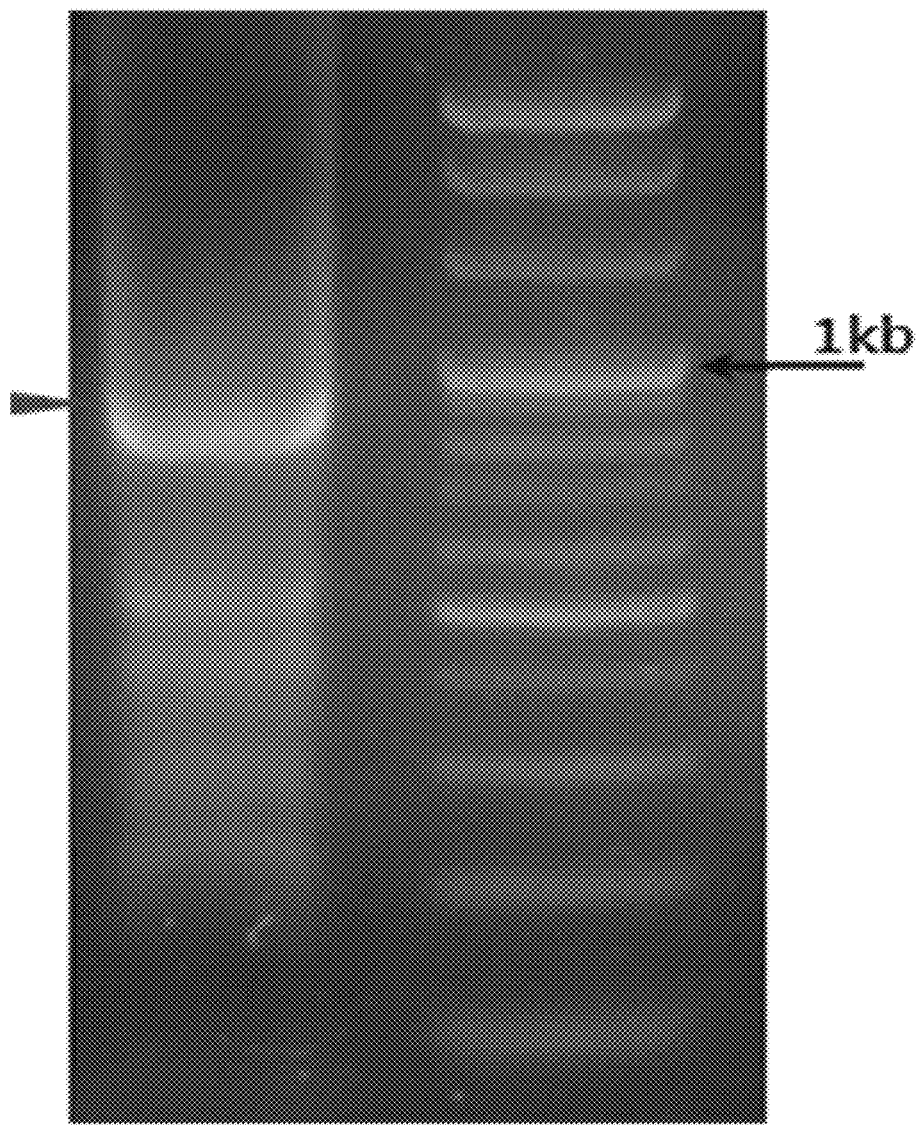

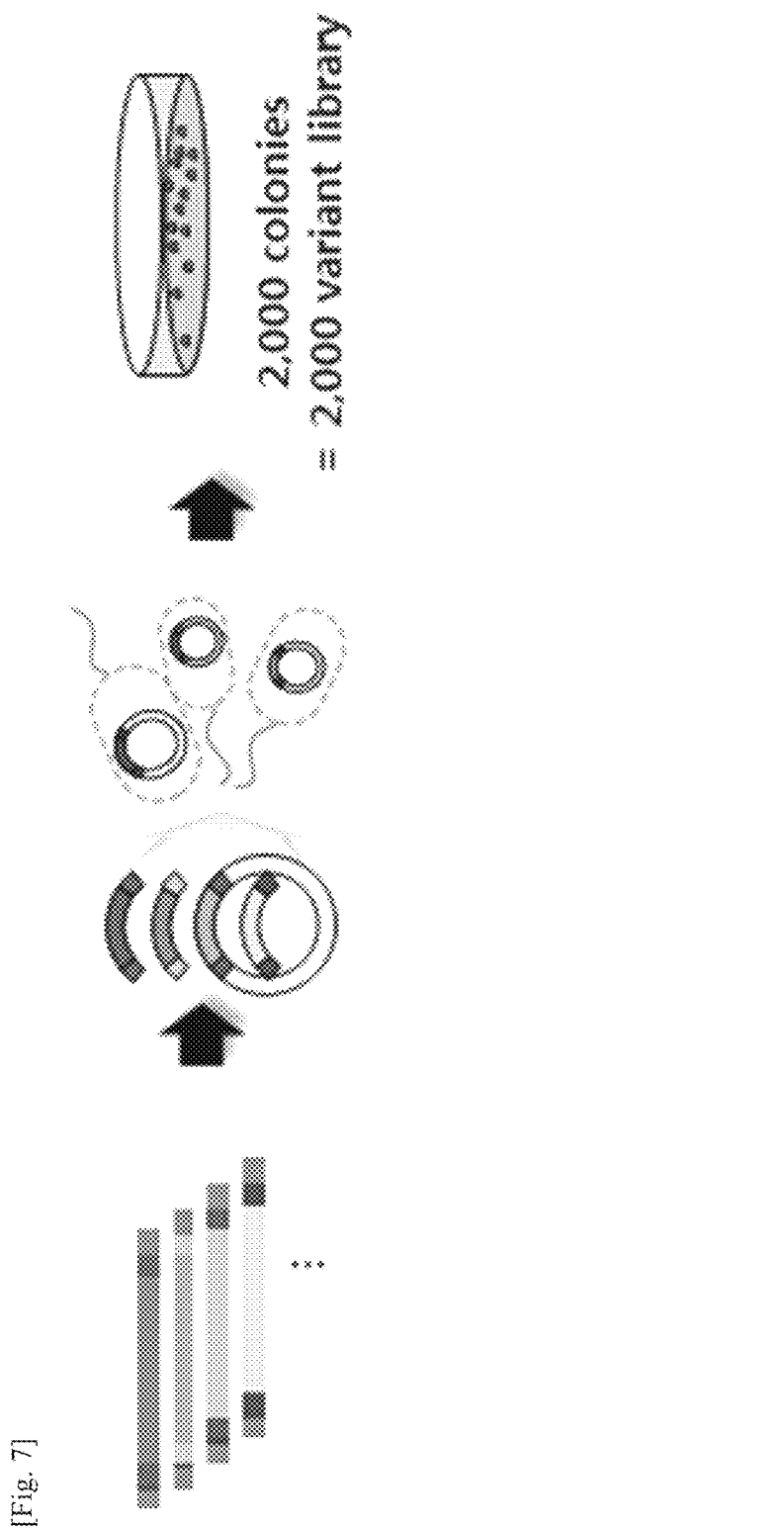
[Fig. 7]

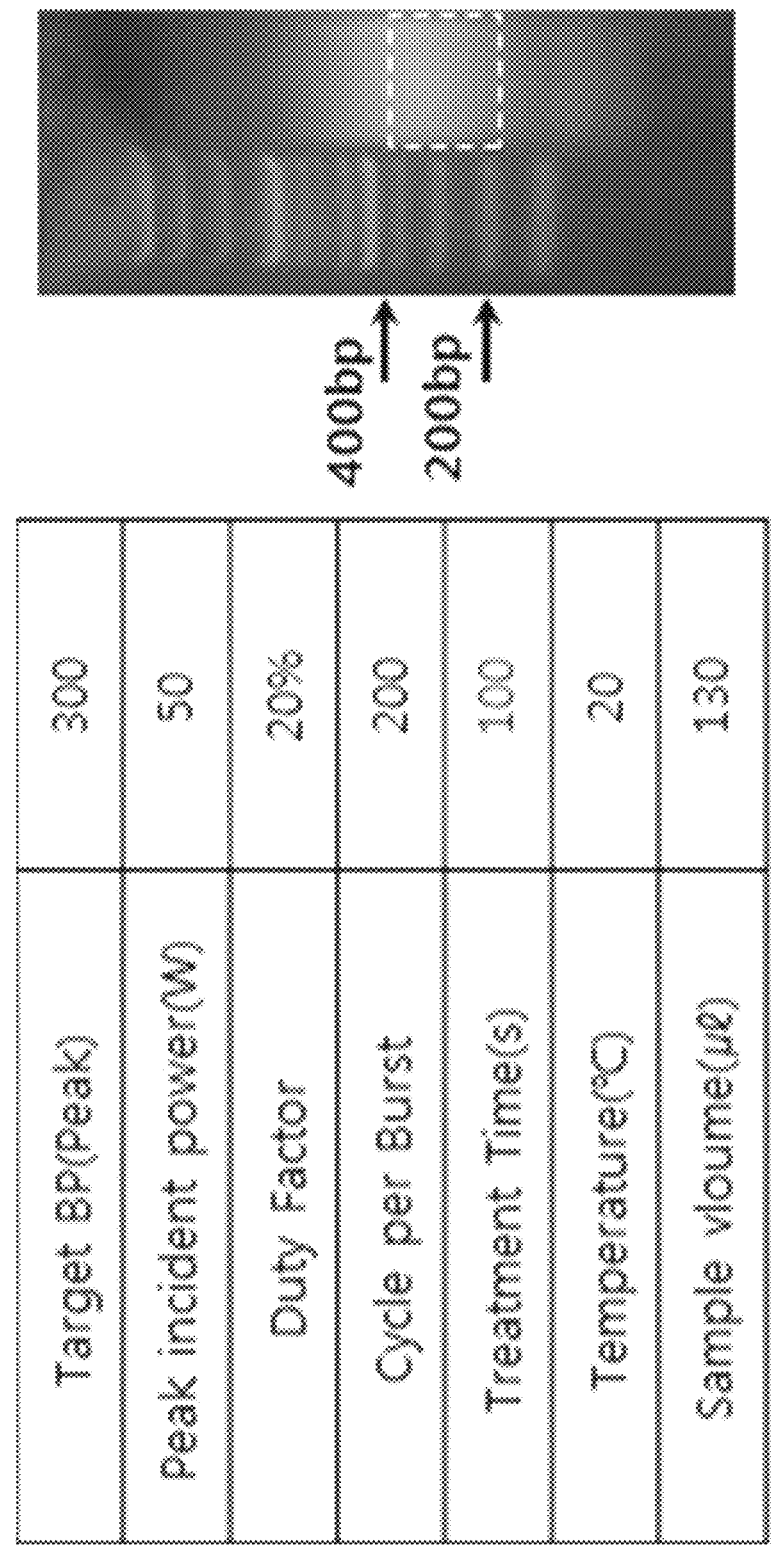
[Fig. 8]

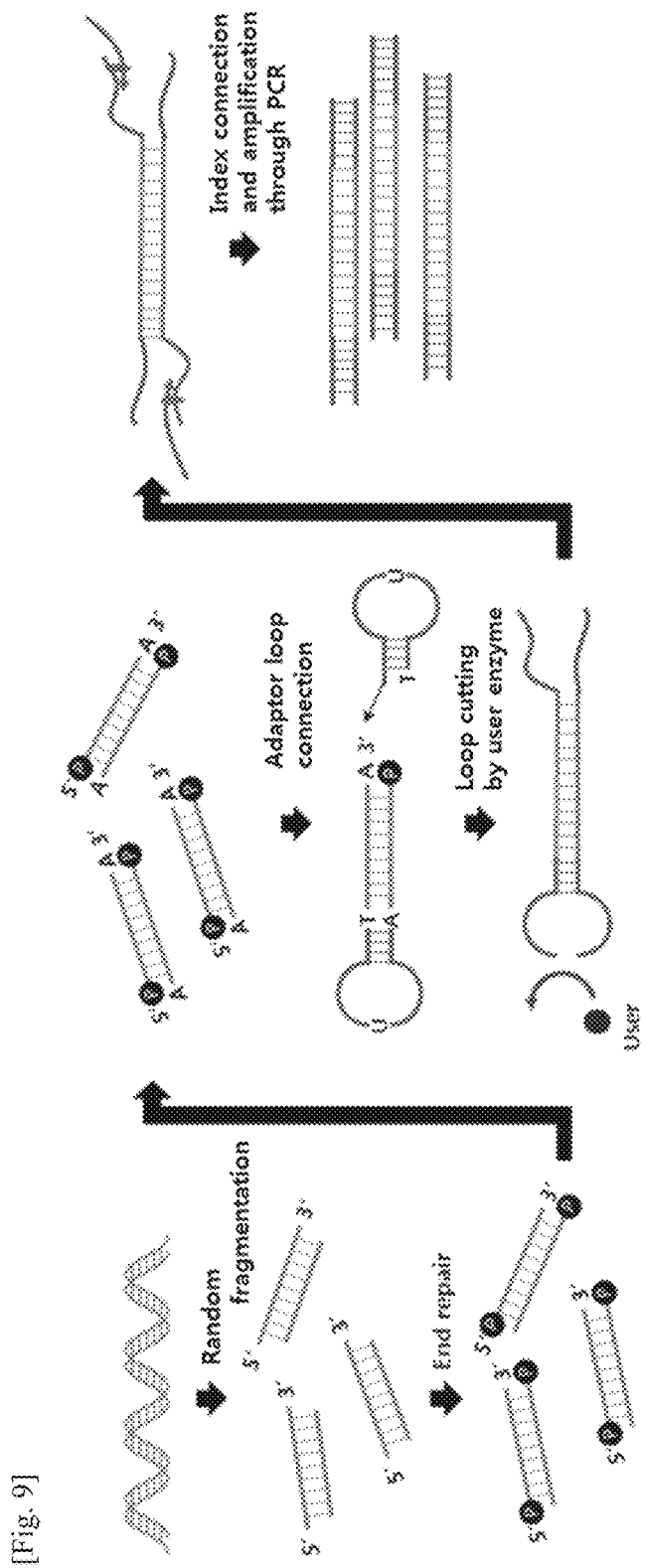
[Fig. 9]

[Fig. 10]

[Fig. 11]
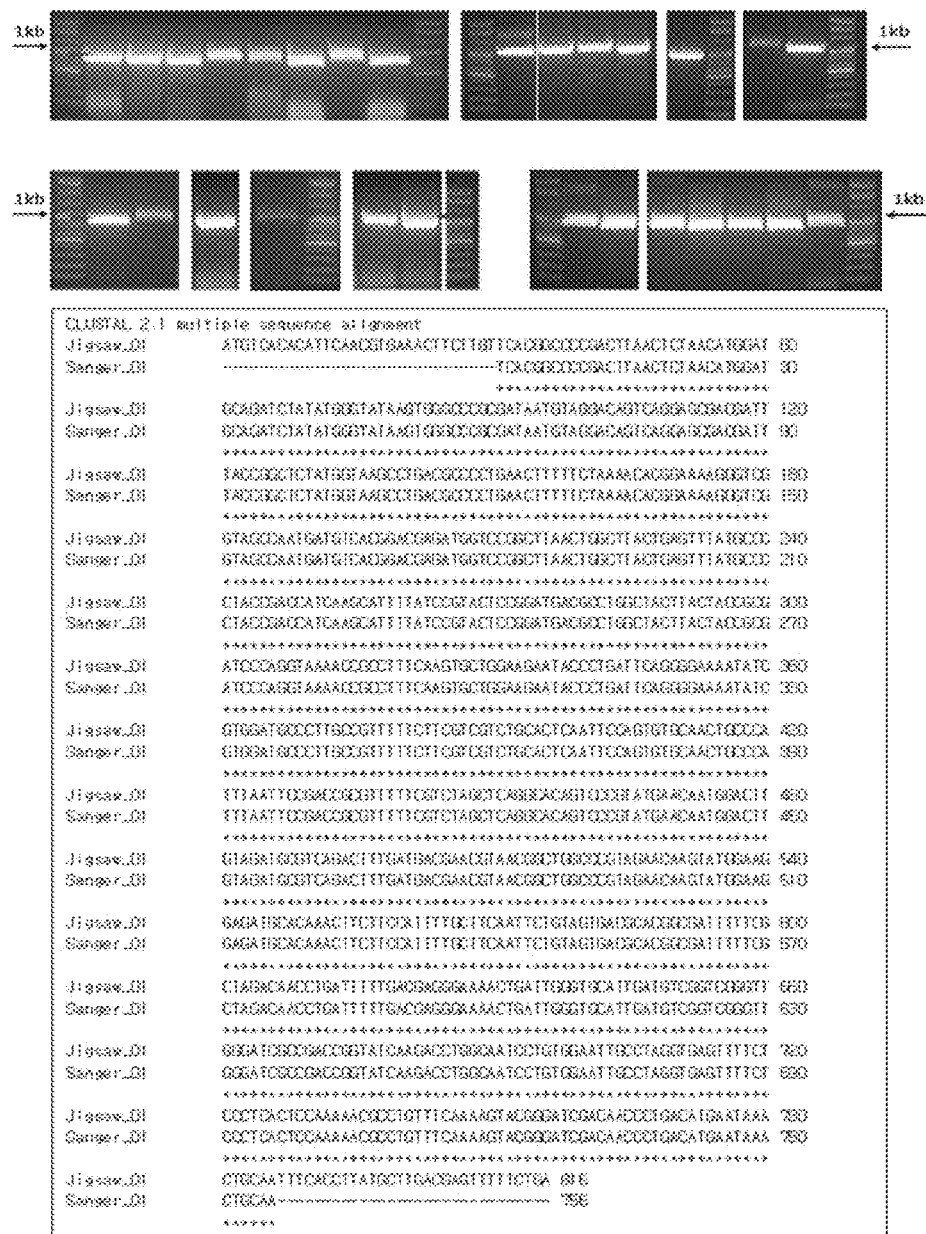

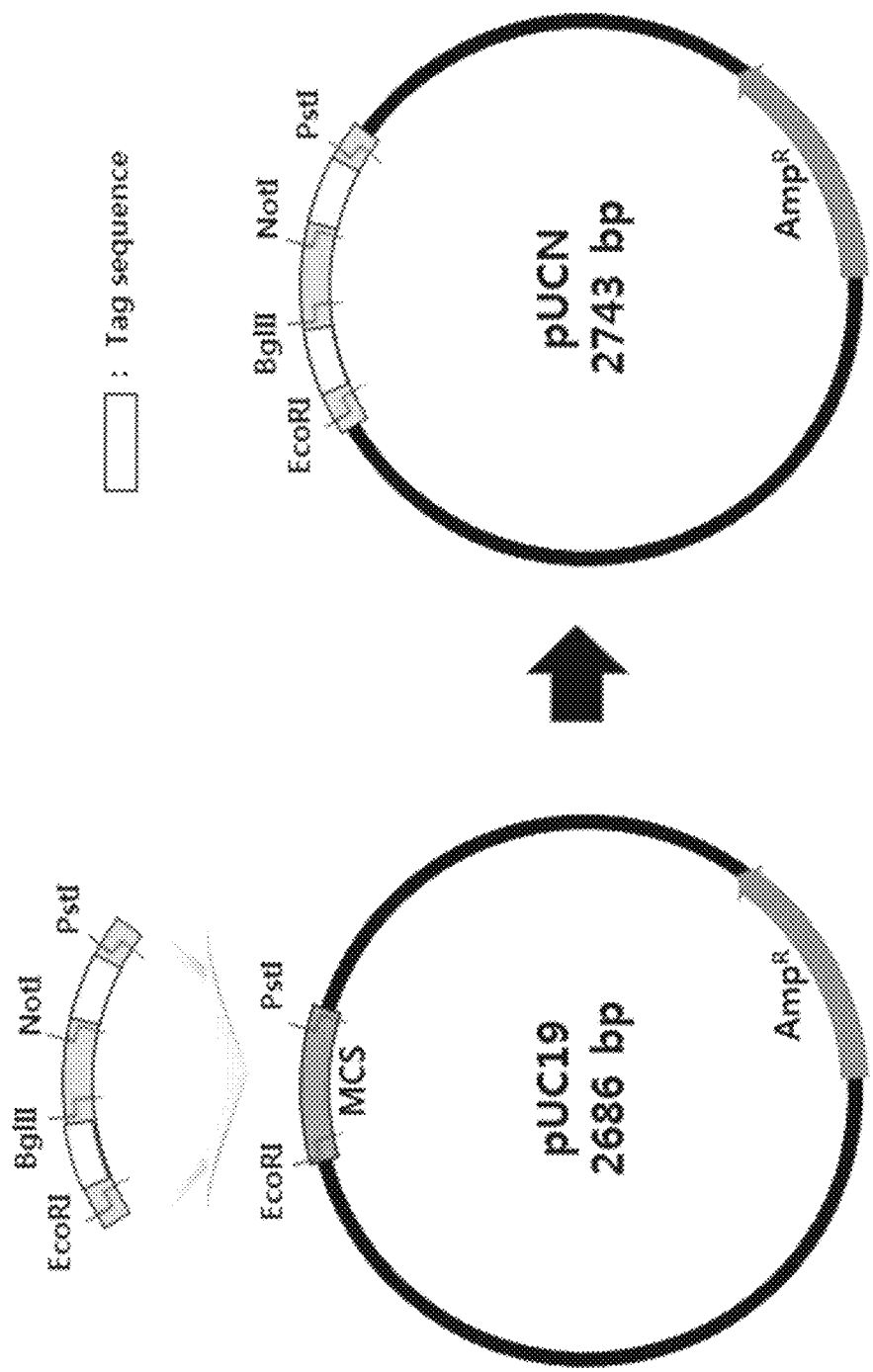
[Fig. 12]

[Fig. 13]
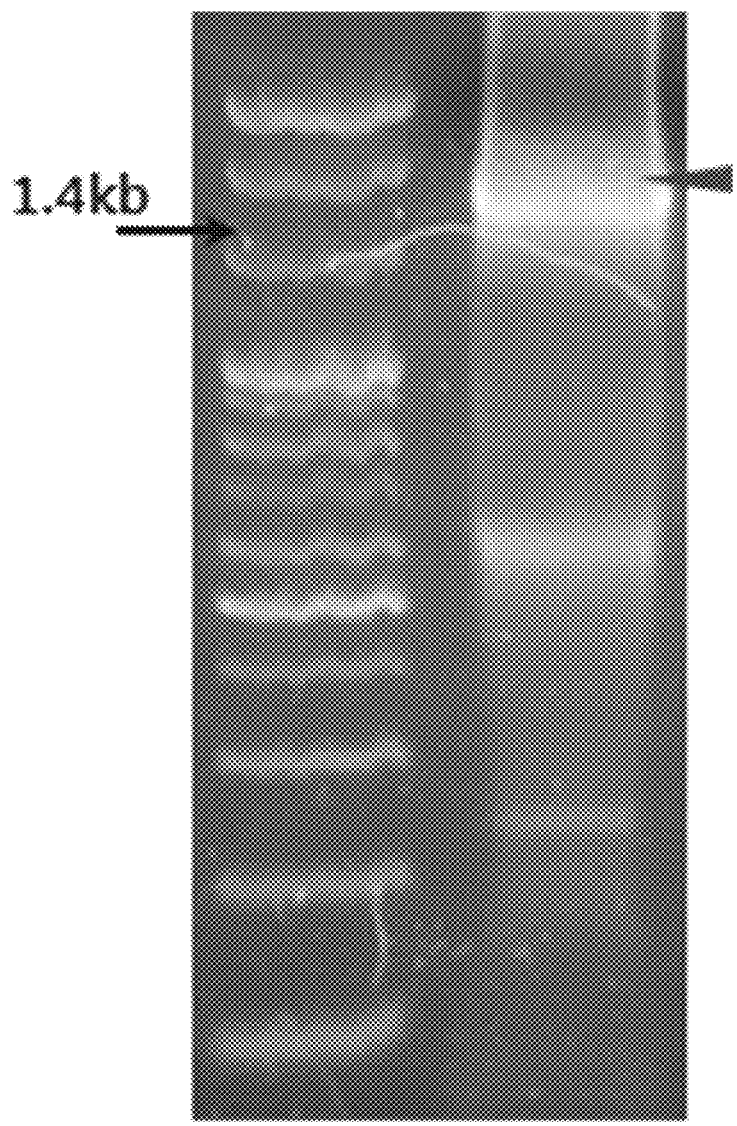

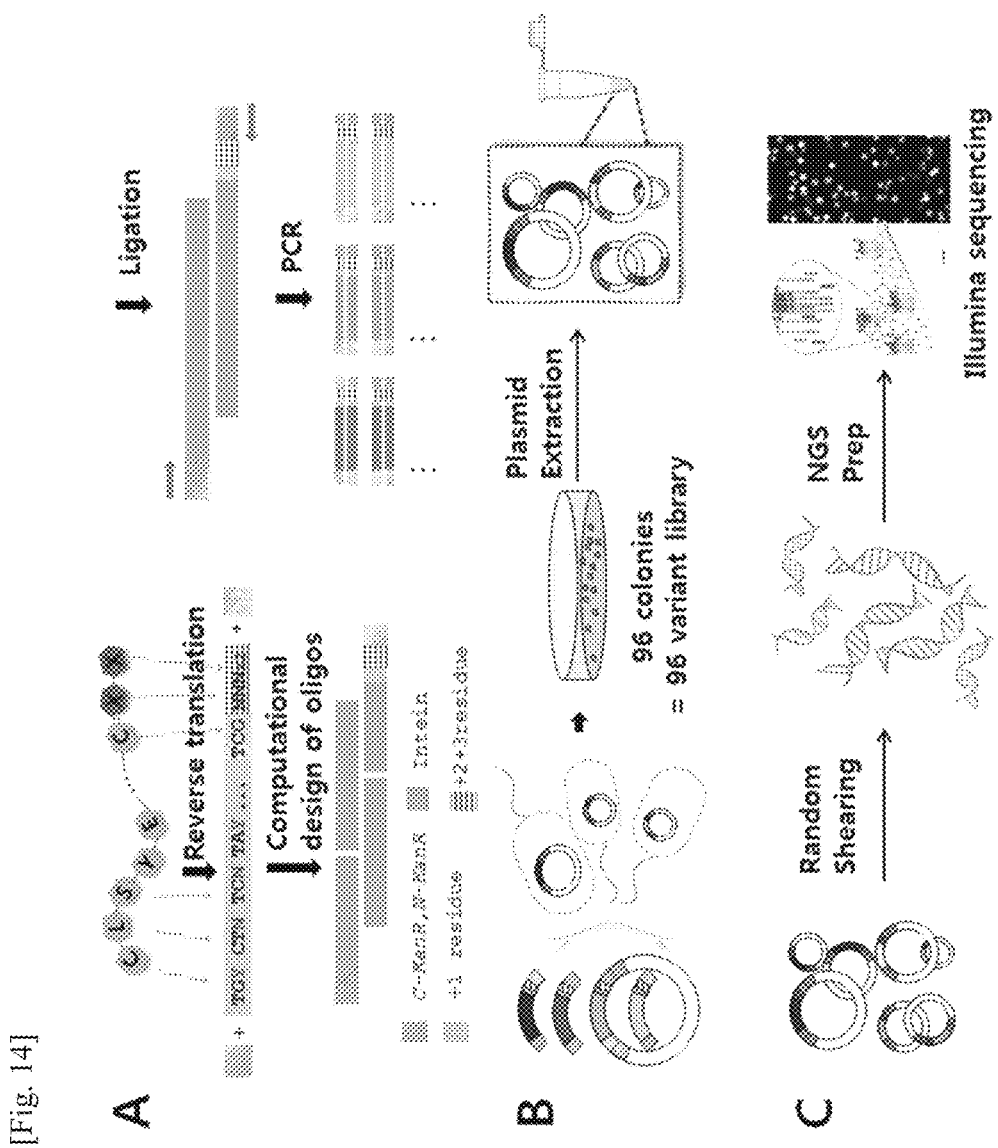
[Fig. 14]

[Fig. 15]

[Fig. 16]
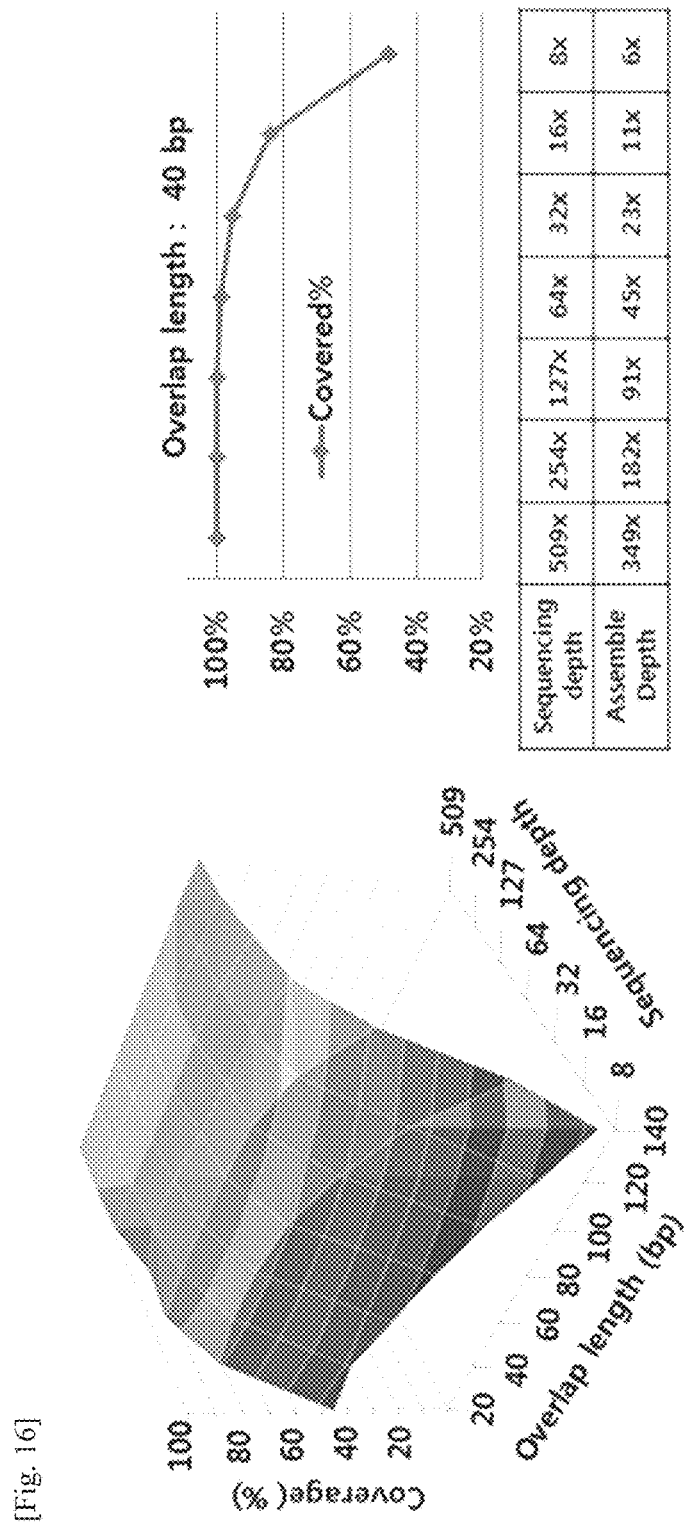

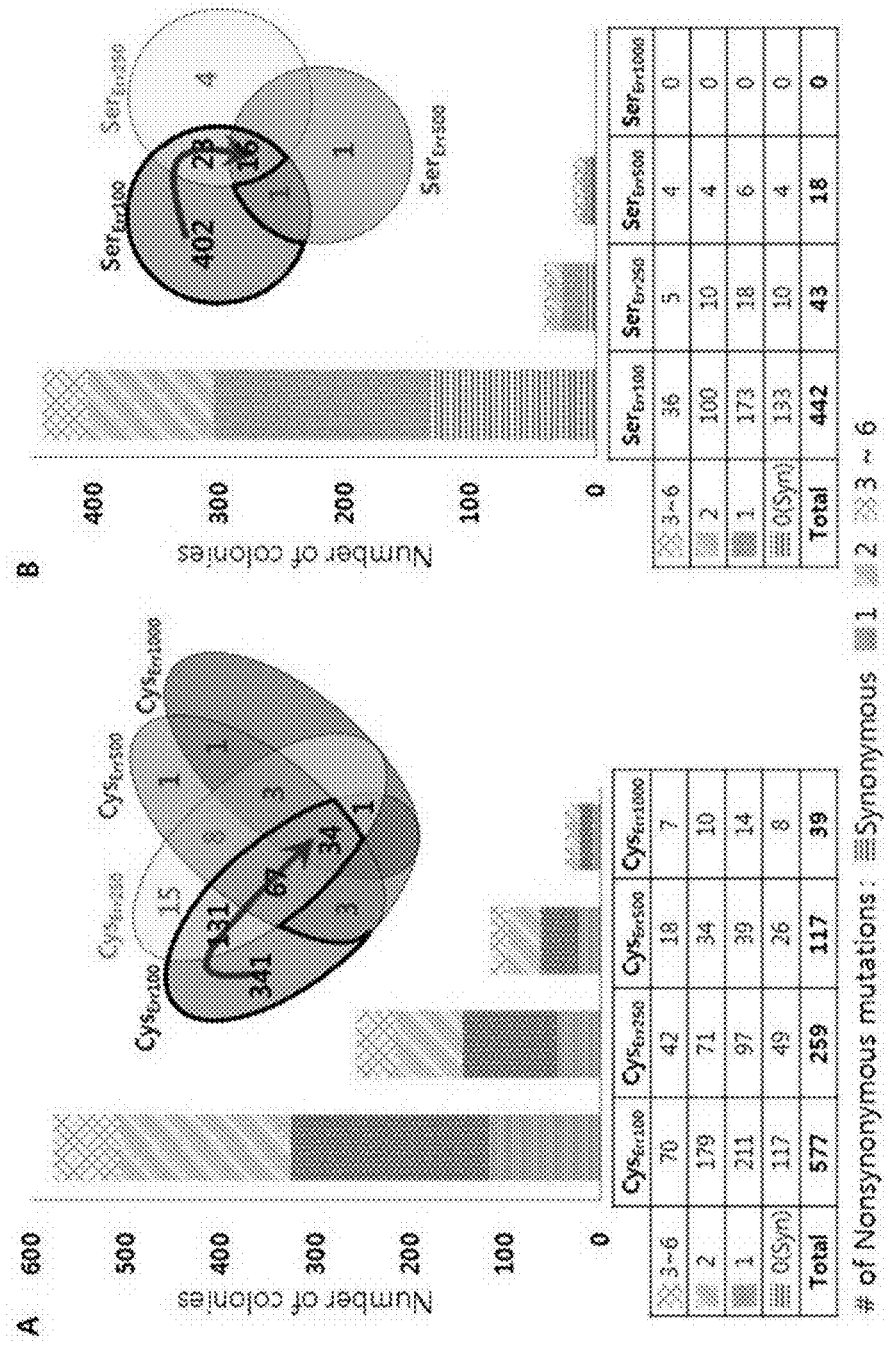
[Fig. 17]

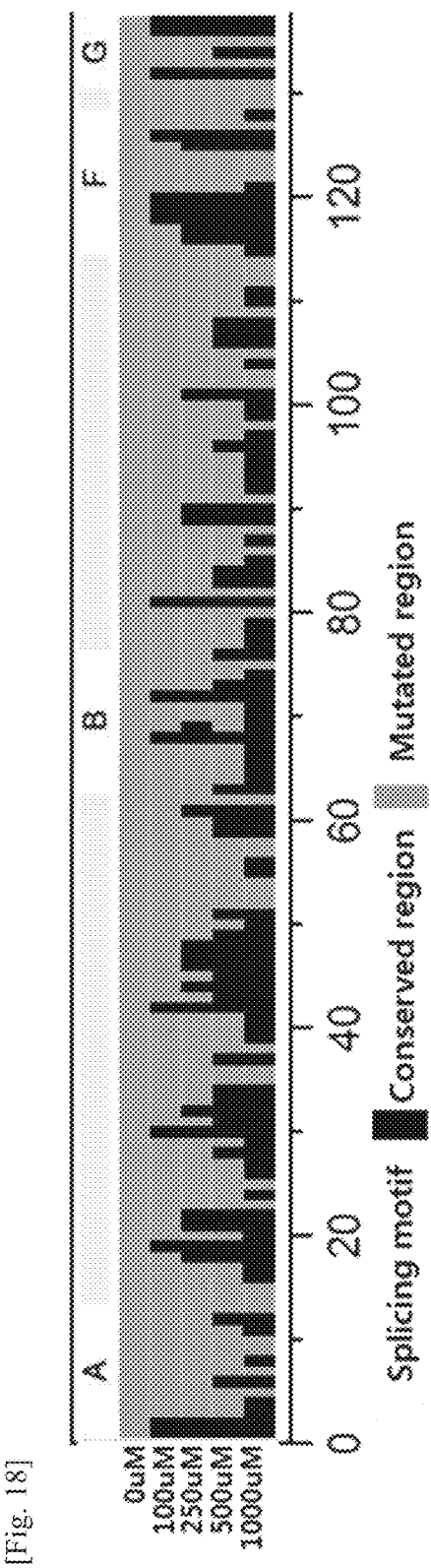
[Fig. 18]

[Fig. 19]

| CysEcr | 0μM | 100μM | Frequency (%) 250μM | 500μM | 1000μM | p-value |
|---|---|---|---|---|---|---|
| X140E | 3.97 | 17.61 | 25.71 | 38.46 | 48.39 | 6.32E-21 |
| X140D | 3.61 | 18.91 | 30.00 | 37.36 | 45.16 | 6.79E-21 |
| X139W | 0.00 | 1.96 | 4.29 | 0.79 | 12.90 | 1.09E-08 |
| X139Y | 3.61 | 10.87 | 13.33 | 16.48 | 32.26 | 3.40E-08 |
| X139F | 0.00 | 0.43 | 1.43 | 3.30 | 9.68 | 1.92E-06 |
|  | 2.89 | 8.70 | 9.05 | 15.38 | 22.58 | 7.29E-06 |
|  | 0.00 | 0.87 | 1.43 | 3.30 | 6.45 | 2.71E-04 |
|  | 0.00 | 1.30 | 2.86 | 3.30 | 6.45 | 3.74E-04 |
|  | 0.00 | 0.65 | 0.95 | 2.20 | 6.45 | 6.78E-04 |
|  | 0.00 | 0.87 | 0.95 | 2.20 | 6.45 | 1.36E-03 |
|  | 0.00 | 0.22 | 0.48 | 2.20 | 3.23 | 1.81E-03 |
|  | 0.00 | 0.43 | 0.95 | 2.20 | 6.45 | 2.16E-03 |
|  | 0.00 | 0.43 | 0.95 | 2.20 | 3.23 | 4.12E-03 |
|  | 0.36 | 0.65 | 0.48 | 2.20 | 3.23 | 8.88E-03 |
|  | 0.00 | 0.22 | 0.22 | 1.10 | 3.23 | 9.57E-03 |
|  | 0.00 | 0.22 | 0.48 | 1.10 | 3.23 | 9.57E-03 |

| SerEcr | 0μM | 100μM | Frequency (%) 250μM | 500μM | p-value |
|---|---|---|---|---|---|
| X140D | 3.49 | 30.42 | 57.58 | 71.43 | 2.00E-42 |
| X139F | 3.31 | 10.36 | 18.18 | 42.86 | 1.08E-11 |
|  | 0.00 | 0.65 | 3.03 | 14.29 | 8.96E-08 |
|  | 0.37 | 2.59 | 9.09 | 14.29 | 1.35E-07 |
| X139M | 0.00 | 1.62 | 6.06 | 7.14 | 4.07E-06 |
| X139Y | 1.47 | 5.50 | 9.09 | 14.29 | 1.36E-05 |
|  | 3.31 | 8.41 | 12.12 | 21.43 | 1.47E-05 |
|  | 0.00 | 0.65 | 3.03 | 7.14 | 6.28E-05 |
|  | 0.92 | 1.29 | 9.09 | 14.29 | 7.00E-05 |
|  | 0.00 | 0.97 | 3.03 | 7.14 | 7.66E-05 |
|  | 0.18 | 0.65 | 6.06 | 7.14 | 7.70E-05 |
|  | 0.18 | 0.65 | 3.03 | 7.14 | 1.12E-03 |
|  | 0.18 | 0.32 | 3.03 | 7.14 | 1.26E-03 |
|  | 0.18 | 0.32 | 3.03 | 7.14 | 1.26E-03 |

☐ : Mutation on Intein residue  
▓ : Mutation on Extein residue

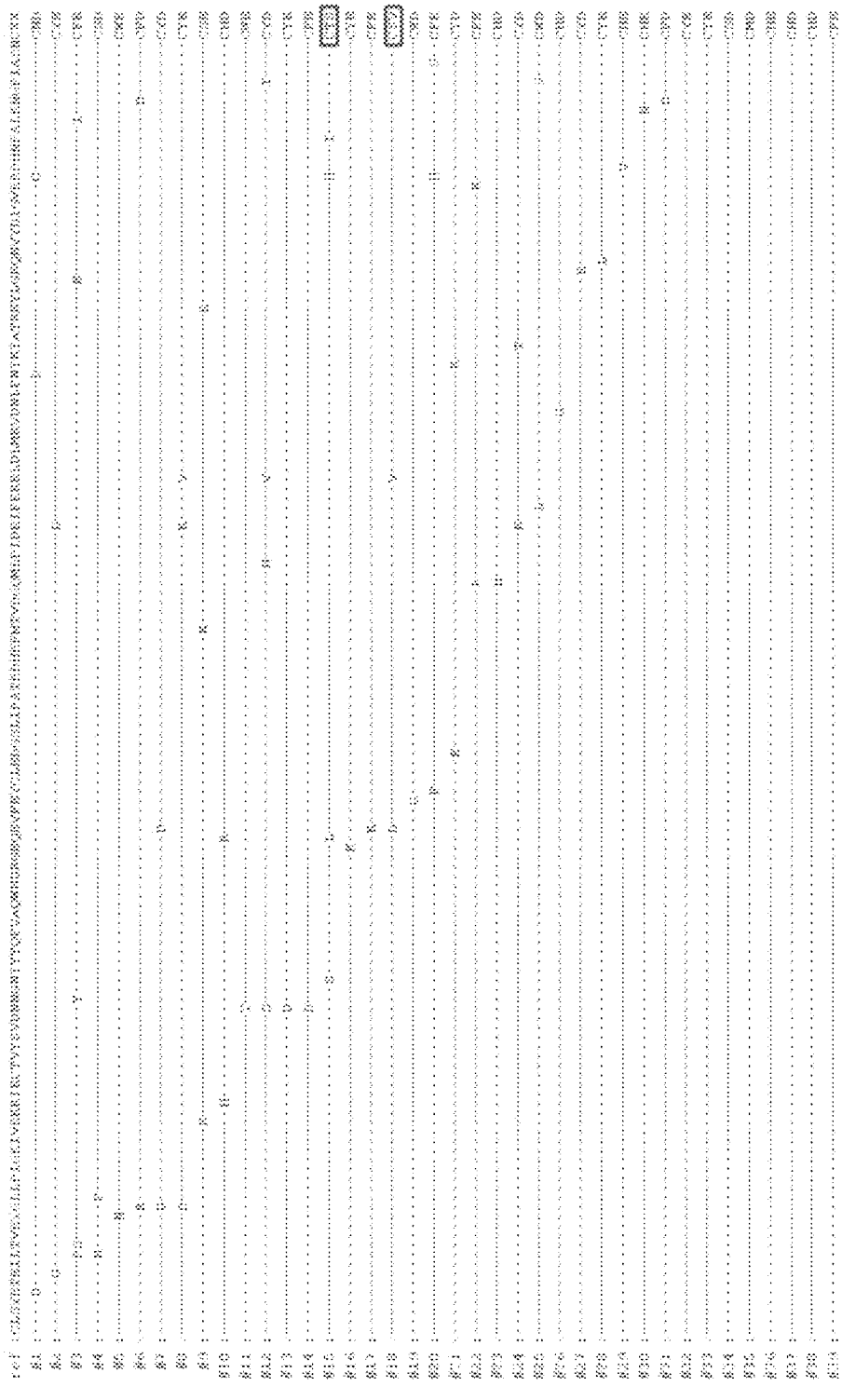
[Fig. 20]

[Fig. 21]

[Fig. 22]
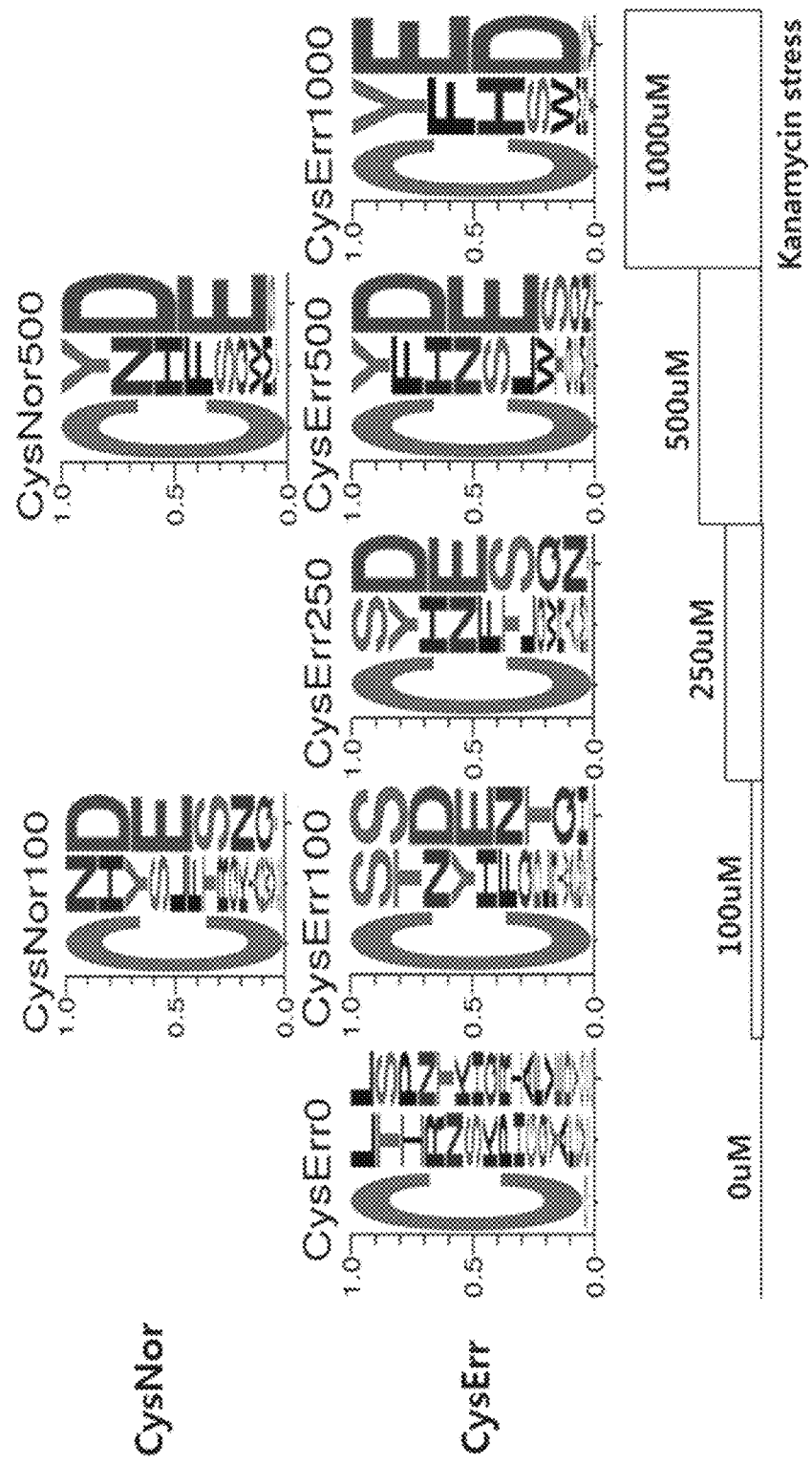

[Fig. 23]
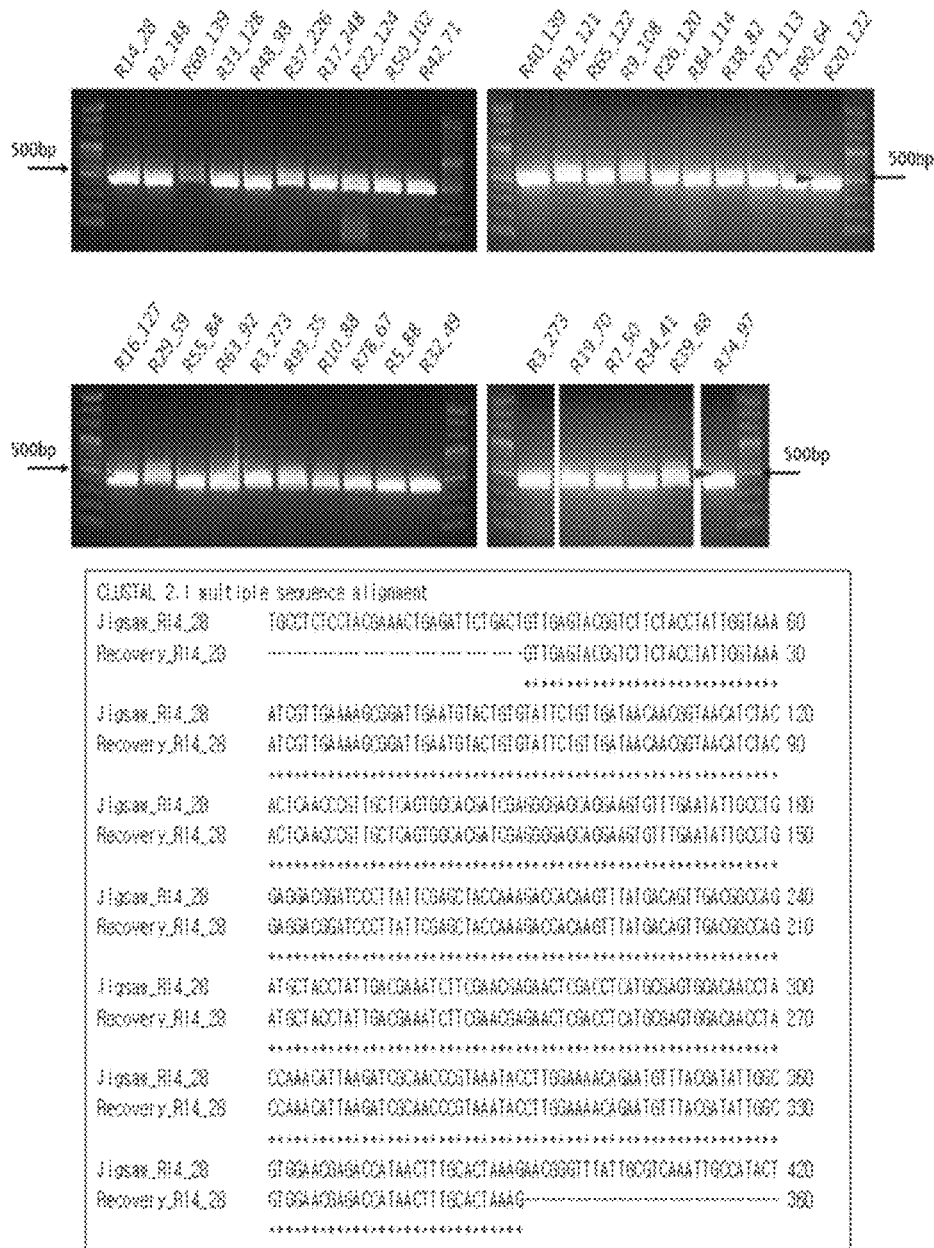

US 10,036,007 B2

METHOD OF SYNTHESIS OF GENE LIBRARY USING CODON RANDOMIZATION AND MUTAGENESIS

CROSS REFERENCE TO PRIOR APPLICATIONS

This application is a National Stage Application of PCT International Patent Application No. PCT/KR2013/011492 filed on Dec. 11, 2013, under 35 U.S.C. § 371, which claims priority to Korean Patent Application No. 10-2012-0143980 filed on Dec. 11, 2012, which are all hereby incorporated by reference in their entirety.

TECHNICAL FIELD

The present disclosure relates to a method of easily synthesizing and analyzing a gene library and a sequence library having genetic mutations of proteins.

BACKGROUND ART

In general, gene synthesis means technology of synthesizing long nucleic acid fragments, the lengths of which are 200 base pairs (bp) or more, including genetic information from oligonucleotides as short nucleic acid fragments. To do this, software for designing oligonucleotides for gene synthesis, oligonucleotide synthesis and gene assembly technology using oligonucleotides are necessary. As general oligonucleotide synthesis methods, there are a solid-phase oligo synthesis method, and an oligo synthesis method using a DNA microarray. Methods of assembling oligonucleotides may be broadly classified into three methods, namely, assembly PCR, fusion PCR and ligase chain reaction (LCR) followed by fusion PCR. Synthesized genes must be sequence verified so as to find errors caused by synthesis and assembly of oligonucleotides and to only select nucleic acid fragments having exact genetic information.

Conventional gene synthesis has been performed by dividing exact nucleic acid base sequences of a gene into a variety of short oligonucleotides to synthesize the gene and, after assembling the divided oligonucleotides, selectively retrieving genes having exact nucleic acid base sequences by evaluating through Sanger sequencing (Mol Biosyst. 2009 July; 5(7):714-22. doi: 10.1039/b822268c. Epub 2009 Apr. 6). However, such a method has a limitation due to absence of proper sequencing technology despite the development of various assembly technologies. Recently, thanks to the development of a variety of next-generation sequencing technologies, (for example, various technologies such as Illumina technology, Ion Torrent technology, and 454 technology), the amount of processed sequence information is exponentially increasing and analysis costs are also gradually falling (Carr, P. A. and Church, G. M. (2009) Genome engineering. Nat. Biotechnol., 27, 1151-1162). Although high throughput verification of short oligonucleotides became possible due to the development of next-generation sequencing (NGS) methods, effective use in a final estimation step after completing synthesis was impossible due to a limitation, namely, a short read length, inherent in the next generation sequencing. Since the next generation sequencing has a drawback that a read length of nucleic acid base sequences capable of being analyzed in a batch is short, a synthesized gene goes through a random fragmentation or random shearing process in which the synthesized gene is divided into short fragments again and analysis of the resultant gene is initiated using a next generation sequencer. Subsequently, sequences derived from the next generation sequencer are analyzed and then, using the analyzed result, the DNA fragments are assembled into whole gene sequences by computer software. Such a process has a limitation that it is difficult to judge errors occurring during gene synthesis and nucleic acids sequencing are derived from which fragments. In addition, when the length of a synthesized gene is not long and the kinds of analyzed gene library is small, a method of analyzing a synthesized gene using the next generation sequencing is not an economical method. As such, utilization of the next generation sequencing in gene synthesis is extremely limited.

Broadly understanding a correlation between phenotypes and genotypes of proteins is a very important research subject in protein engineering or biosynthetic pathway engineering. In practice, after engineering a promoter (Patwardhan R P, Lee C, Litvin O, Young D L, Pe'er D, Shendure J. Nature Biotechnology, 27, 1173-1175 (2009)), a short peptide (Whitehead T A, Chevalier A, Song Y, Dreyfus C, Fleishman S J, De Mattos C, Myers C A, Kamisetty H, Blair P, Wilson I A, Baker D. Nature Biotechnology, 30, 543-548 (2012)), a complementarity determining region of a single chain antibody (DeKosky B J, Ippolito G C, Deschner R P, Lavinder J J, Wine Y, Rawlings B M, Varadarajan N, Giesecke C, Dorner T, Andrews S F, Wilson P C, Hunicke-Smith S P, Willson C G, Ellington A D, Georgiou G. Nature Biotechnology, 31, 166-169 (2013), Larman H B, Xu G J, Pavlova N N, Elledge S J. PNAS, 109, 18523-18528 (2012)), research to determine a correlation between phenotypes and genotypes in the engineered sequence has been continuously performed. However, such research does not commonly target a total region of a protein due to a short read length in next generation sequencing, and an short domain region than a read length can be engineered. So as to engineer the total region of a protein, library must be sequenced through Sanger sequencing or next generation sequencing information (short reads) must be reassembled. The former case is very inefficient since it is time-consuming and laborious, and large costs are required. The latter case is prohibited by currently known methods.

DISCLOSURE

Technical Problem

Therefore, the present disclosure has been made in view of the above problems, and it is an object of the present disclosure to provide a method of synthesizing a gene and engineering a total region of a protein by resolving limitations of next generation sequencing.

Technical Solution

In accordance with an aspect of the present disclosure, the above and other objects can be accomplished by the provision of a method of synthesizing a second gene library, the method comprising (a) providing a first gene library comprising randomized codons encoding to a specific protein sequence but having different nucleic acid base sequences, (b) fragmenting the first gene library into nucleic acid fragments, (c) confirming base sequences of the nucleic acid fragments, and (d) reassembling the base sequence-confirmed nucleic acid fragments into gene sequences before fragmentation using the codon-randomized base sequences.

In accordance with another aspect of the present disclosure, there is provided an error-free gene library comprising genes encoding the same protein but having different base sequences, manufactured by the method described above.

In accordance with another aspect of the present disclosure, there is provided a method of synthesizing a library of mutated genes, the method comprising (a) providing a gene library comprising randomized codons encoding to a specific protein sequence but having different nucleic acid base sequences, (b) inducing mutagenesis of the gene library, (c) fragmenting the mutated gene library into nucleic acid fragments, (d) confirming base sequences of the nucleic acid fragments; and (e) reassembling the base sequence-confirmed nucleic acid fragments into gene sequences before fragmentation using codon-randomized base sequences.

In accordance with another aspect of the present disclosure, there is provided a library of mutated genes manufactured by the method of synthesizing the library of the mutated genes described above.

In accordance with yet another aspect of the present disclosure, there is provided a method of selectively amplifying desired gene sequences from the library of the mutated genes described above.

Advantageous Effects

According to the present disclosure, when next generation sequencing is performed by fragmenting a gene, original gene sequences may be exactly recovered by assembling NGS reads through overlap-consensus approach. Through this, a limitation (short read length) of next generation sequencing when applied to gene synthesis may be addressed. In addition, several hundred to thousands of different gene libraries including identical protein information and different DNA sequences (synonymous gene library) may be manufactured in a batch, and all gene sequences may be confirmed by sequencing once. When such a gene library synthesis and analysis method is combined with a protein engineering method, engineering for an entire region of a protein, which is impossible in a conventional method, becomes possible.

DESCRIPTION OF DRAWINGS

The above and other objects, features and other advantages of the present disclosure will be more clearly understood from the following detailed description taken in conjunction with the accompanying drawings, in which:

FIG. 1 is a flowchart illustrating a method of synthesizing a gene library according to one embodiment of the present disclosure;

FIG. 2 is a view illustrating a process of deriving DNA sequences of randomized codons by protein sequences of a target gene according to one embodiment of the present disclosure;

FIG. 3 is a view illustrating oligonucleotide design to synthesize a gene library according to one embodiment of the present;

FIG. 4 is a schematic diagram illustrating removal of a plasmid backbone using a restriction enzyme and next generation sequencing according to one embodiment of the present disclosure;

FIG. 5 is a schematic diagram illustrating a process of reassembling nucleic acid fragments sequenced through next generation sequencing according to one embodiment of the present disclosure;

FIG. 6 is a view illustrating a synthesis result of a kanR gene library according to one embodiment of the present disclosure;

FIG. 7 is a schematic diagram illustrating control of a gene library size in transformation using *E. coli* according to one embodiment of the present disclosure;

FIG. 8 is a view illustrating a condition and a result of random fragmentation using an ultrasonicator according to one embodiment of the present disclosure;

FIG. 9 is a view illustrating a preparation process for next generation sequencing after fragmentation according to one embodiment of the present disclosure;

FIG. 10 is a view illustrating an analysis result for a kanR gene library according to one embodiment of the present disclosure;

FIG. 11 is a view illustrating a result of a selective recovery experiment for a kanR gene library according to one embodiment of the present disclosure;

FIG. 12 is a view illustrating preparation of a pUCN plasmid using a pUC19 plasmid according to one embodiment of the present disclosure;

FIG. 13 is a view illustrating a synthesis result of a tolC gene library according to one embodiment of the present disclosure;

FIG. 14 is a view illustrating a preliminary experimental process using Npu intein according to one embodiment of the present disclosure;

FIG. 15 is a view illustrating an analysis result of an experiment using Npu intein according to one embodiment of the present disclosure;

FIG. 16 is a view illustrating a simulation result for experimental data using Npu intein according to one embodiment of the present disclosure;

FIG. 17 is a view illustrating summarized information for analysis of a mutated Npu intein library according to one embodiment of the present disclosure;

FIG. 18 is a schematic diagram illustrating highly conserved locations of Npu intein according to one embodiment of the present disclosure;

FIG. 19 is a view representing preferred mutations calculated through a trend test according to one embodiment of the present disclosure;

FIG. 20 is a view illustrating genotypes of a CysErr1000 pool according to one embodiment of the present disclosure;

FIG. 21 is a view illustrating a tolerance degree to kanamycin of intein mutants according to extein types according to one embodiment of the present disclosure;

FIG. 22 is a view illustrating extein residue tendencies in a CysErr pool and a SerErr pool according to one embodiment of the present disclosure; and FIG. 23 is a view illustrating results for a selective recovery experiment of Npu intein according to one embodiment of the present disclosure.

BEST MODE

The term "nucleotide" as used in the present specification means single or double-strand deoxyribonucleic acid (DNA) or ribonucleic acid (RNA), and, so long as not defined otherwise, may include analogues of a nucleotide.

The term "amplification", as used in the present disclosure, means reaction of amplifying target nucleic acid base sequences and may be performed using polymerase chain reaction (PCR). The PCR includes, but is not limited to, reverse transcription polymerase chain reaction (RT-PCR), multiplex PCR, real-time PCR, assembly PCR, fusion PCR and ligase chain reaction (LCR).

The term "primer", as used in the present disclosure, means an oligonucleotide. The primer is a single strand, may include ribonucleic acid, and is preferably deoxyribonucleic acid. The primer is hybridized or annealed to one strand of a template, thereby forming a double stranded structure. The primer may be hybridized or annealed to the flanking sequences of the present disclosure. The term "annealing" means that oligonucleotides or nucleic acids are juxtaposed with template nucleic acids, and by the juxtaposition, nucleotides are polymerized through a polymerase, thus, nucleic acid molecules complementary to template nucleic acids or a portion thereof are formed. The term "hybridization" means that two single stranded nucleic acids form a duplex structure via pairing of complementary sequences. The primer may function as an initiator of synthesis when a synthesis of an extended product of a primer complementary to a template is induced.

In the present disclosure, 5' terminal flanking sequences and 3' terminal flanking sequences present in terminals of oligonucleotides are priming locations to increase the amount of oligonucleotides, may be used as annealing sites of a primer set to produce a sufficient amount of oligonucleotides, and flanking sequences of both ends may be present in terminals of recognition sequences of restriction enzymes or may include restriction enzyme recognition sequences. In one embodiment of the present disclosure, the flanking sequences of the present disclosure may be used in an amplification reaction.

The term "complementary", as used in the present disclosure, means having complementarity that may selectively hybridize the nucleotide sequences described above under specific hybridization or annealing conditions.

The term "assembly", as used in the present disclosure, means to connect to longer nucleic acid fragments by aligning and merging nucleic acid fragments using complementary sequences.

The term "protein engineering", as used in the present disclosure, means to research a variety of properties such as a structure, function, complementarity or stability of each protein by translating each protein after synthesizing novel proteins having desired amino acid sequences different from a wild type protein. The protein engineering is preparing novel and useful proteins by artificially controlling structures of proteins and includes designing proteins.

The term "cloning", as used in the present disclosure, means to introduce a specific gene into a host cell by connecting the specific gene to a vector through gene manipulation technology and massively proliferating using a duplication mechanism of a cell. As a proliferation method, a method using vector DNA derived from a variety of plasmids or phages may be used.

The term "plasmid", as used in the present disclosure, means DNA that is separated from an intracellular chromosome of a bacterium and a plasmid may autonomously proliferate. The plasmid transports a gene when cloned.

The term "vector", as used in the present disclosure, means a DNA molecule that may be duplicated and may transfer foreign DNA such as a gene to a receptor cell. Examples of the vector include plasmids, phages, artificial chromosomes, and the like. In the present specification, "plasmid", "vector" and "plasmid vector" may be used in the same meaning.

The term "sequencing", as used in the present disclosure, means determining an order of base sequences of DNA molecule. In the present specification, "sequencing", "sequence confirmation", "sequence validation", "sequence verification" and "base sequence analysis" may used in the same meaning.

The term "read", as used in the present disclosure, means one nucleic acid fragment analyzed through next generation sequencing. In addition, the term "read length" means the lengths of nucleic acid fragments that may be analyzed in a batch through next generation sequencing.

The term "depth", as used in the present disclosure, means a reading frequency of one nucleotide at one location in a sequencing process. For example, "100×" means that one nucleotide at the same location is repetitively confirmed 100 times.

Hereinafter, the present disclosure will be described in more detail. The following embodiments are provided to sufficiently convey the sprit disclosed in the present disclosure to one of the ordinary skill in the art. Therefore, the present disclosure is not limited to embodiments described below and may be embodied into other forms.

So as to overcome technical limitation of next generation sequencing in gene synthesis and engineer an entire region of a protein using the method, the present researchers developed a novel gene library synthesis and analysis method called "Jigsaw assembly". Jigsaw assembly includes a synthesis process of a codon combination library of a target gene using codon-randomized, a preparation process for next generation sequencing, and a computational analysis process of next generation sequencing data. When codon-randomized DNA sequences are derived using protein sequences of a target gene and then synthesized to a library type, all gene sequences in the library have the same protein information but DNA sequences are not homologous. That is, by lowering homology of DNA sequences of a homologous gene library through codon-randomized, fragmented sequence information may be reassembled. This means that barcoding of each gene sequence itself is possible. Therefore, even when a synthesized whole library is fragmented into short nucleic acid fragments and then next generation sequencing thereof is carried out, gene sequences before fragmentation may be exactly recovered by collecting and connecting nucleic acid fragments sharing the same DNA sequences.

This enables analysis of several thousands of whole (full-length) gene sequences or more in a batch by performing next generation sequencing once. Therefore, the method according to the present disclosure may be used as a gene synthesis method and a selective recovery method of error-free genes, and enables engineering of full-length protein sequences using next generation sequencing. The present disclosure includes gene library synthesis using Jigsaw assembly, analysis through next generation sequencing and development of a method of engineering full-length protein sequences by combining random mutagenesis technology.

FIG. 1 is a flowchart illustrating a method of synthesizing a gene library according to one embodiment of the present disclosure.

Referring to FIG. 1, step S1 provides a first gene library of randomized codons encoding a specific protein sequence but having different nucleic acid base sequences.

20 amino acid types are present in nature but the number of codons translating the amino acids is 64. Therefore, theoretically, one protein sequence may be reversibly translated into a library of similar genes forming a variety of codon combinations. The similar gene library may be synthesized by inserting degenerate nucleotides in an in vitro synthesis process of oligonucleotides. Genes of the synthesized library are translated into an identical protein sequence but DNA sequences thereof are not identical. Therefore, when a corresponding library is fragmented into short nucleic acid fragments and then sequenced, gene sequences before fragmentation can be reassembled by comparing nucleic acid base sequences of overlapping regions of the nucleic acid fragments. This appears to be a puzzle to be assembled and, thus, was named Jigsaw assembly.

In one embodiment of the present disclosure, the codon randomization may be preparing various combinations coding the same amino acid but having different nucleic acid base sequences by inserting degenerate codons into gene sequences coding a specific protein sequence. Referring to FIG. 2, by reestablishing the table for codons used in nature, degenerate sequences such as N (combination of A, T, C and G), R (combination of A and G), Y (combination of T and C), or the like may be inserted into codons translating a specific amino acid in a process of synthesizing oligonucleotides having a portion of gene sequences coding the specific protein sequence. For example, in codons coding the same amino acid, a base position that all of adenine (A), thymine (T), cytosine (C) and guanine (G) are available may be represented by N, a base position that adenine or guanine are available may be represented by R, and a case that thymine or cytosine are available may be represented by Y. For example, as codons that may be translated into alanine, there are GCA, GCT, GCC and GCG, and the codons may be represented by GCN. So as to represent available nucleotides, other alphabet letters except for N, R and Y may be used. To represent available nucleotides, any other marks other than alphabet letters may be used. Through such method, a specific protein sequence may be reversely translated to degenerate nucleic acid base sequences.

In one embodiment of the present disclosure, the first library may be synthesized by assembling oligonucleotides designed based on the degeneration of nucleic acid base sequences. As a method of assembling oligonucleotides, any one selected from the group consisting of assembly PCR, fusion PCR and ligase chain reaction (LCR) may be used, but the present invention is not limited thereto. As a method of assembling the oligonucleotides, a conventional oligonucleotide assembly method may be used. An LCR method among the various gene assembly methods may be used. In one embodiment of the present disclosure, an interval gap may not be present between oligonucleotides in the first gene library.

In one embodiment of the present disclosure, both ends of codon-randomized gene sequences in the first gene library may include at least one selected from the group consisting of barcode tag sequences, restriction enzyme recognition sequences and flanking sequences (See FIG. 3).

In one embodiment of the present disclosure, both ends of the codon-randomized gene sequences assembled with the oligonucleotides in the first gene library may include barcode tag sequences. The barcode tag sequences may be used for selective recovery after sequence validation. A method of recovering a gene using the barcode tag sequences as a primer is disclosed in an existing patent: Duhee Bang, Hwangbeom Kim, Hyojun Han, 2011, 10-2011-0076408, "Shotgun DNA Synthesis for the High-throughput Construction of Large DNA Molecules".

In one embodiment of the present disclosure, both ends of the codon-randomized gene sequences assembled with the oligonucleotides in the first gene library may include restriction enzyme recognition sequences. The restriction enzyme recognition sequences may be used to clone into a plasmid vector. The restriction enzyme recognition sequences may be identical or different. A restriction enzyme recognizing the restriction enzyme recognition sequences, for example, may be EcoR I or Hind III, but the present invention is not limited thereto. The restriction enzyme recognition sequences are dependent upon vector types used in cloning.

In one embodiment of the present disclosure, both ends of the codon-randomized gene sequences assembled with the oligonucleotides in the first gene library may include flanking sequences. A primer may be annealed to the flanking sequences during PCR amplification.

In one embodiment of the present disclosure, in a step of providing the codon randomized gene library, sense oligonucleotides may be designed based on upper sequences of double stranded DNA sequences of the target gene and nonsense oligonucleotides may be designed based on lower sequences of double stranded DNA sequences of the target gene. Synthesis may be carried out such that terminal portions of the sense oligonucleotides and the nonsense oligonucleotides overlap. The portions where the sense oligonucleotides and the nonsense oligonucleotides are overlapped may have complementary sequences. In one embodiment of the present disclosure, the lengths of the sense oligonucleotides and the nonsense oligonucleotides may be 100 to 200 bp. In one embodiment of the present disclosure, the lengths of the overlapped portions may be 50 to 150 bp.

In one embodiment of the present disclosure, the sense oligonucleotides and nonsense oligonucleotides may be annealed using overlapping complementary sequences of terminal portions of the oligonucleotides. When temperature of the oligonucleotides is elevated to 95° C. and then slowly lowered, the complementary sense oligonucleotides and nonsense oligonucleotides are annealed with each other. At this time, gaps between the oligonucleotides may be filled with a ligase. The ligase may be a thermo-stable ligase. Through this, a template form for PCR can be completed.

In one embodiment of the present disclosure, the first gene library in which codons are randomized may be provided by amplifying the aligned oligonucleotides. The amplification may be a method of performing PCR using common flanking sequences, which are included when oligonucleotides are designed, of both ends, as primer sequences.

In one embodiment of the present disclosure, after the step of providing the codon randomized first gene library, controlling the number of codon-randomized gene sequences in the first gene library to a verifiable number through next generation sequencing may be further included. The amount of data obtainable in a batch through next generation sequencing is tens of billions of base pairs but, to exactly analyze through high depth taking advantage of next generation sequencing, proper limitation of the size of a synthesized gene library is necessary. In one embodiment of the present disclosure, to limit the number of the gene sequences, cloning using a plasmid and transformation using *E. coli* may be used.

Both ends of the codon-randomized gene sequences may include restriction enzyme recognition sequences. When the codon-randomized first gene library and plasmid vectors are substantially simultaneously double digested using the restriction enzyme and ligated, a plasmid library in which only one codon-randomized gene sequence type is inserted into one plasmid may be prepared. When the plasmid library is transformed into *E. coli*, one cell probabilistically uptakes one plasmid type. Therefore, when the number of *E. coli* cells is limited, the number of the codon-randomized gene sequences is limited. By limiting the number of colonies after culturing the transformed *E. coli* on a solid medium, the number of the codon-randomized gene sequences may be limited and the entire size of the first gene library may be decreased.

In step S2 of FIG. 1, the first gene library is fragmented into nucleic acid fragments.

After purifying plasmids from *E. coli*, the number of which is limited, they are randomly fragmented and next generation sequencing may be performed. In one embodiment of the present disclosure, the fragmenting may be a method of randomly fragmenting entire plasmid vectors including the codon-randomized gene sequences. When whole vectors are fragmented, bias occurred during amplification by PCR may be removed and, thus, more even data than a conventional method may be obtained.

In another embodiment of the present disclosure, the fragmenting may be a method of randomly fragmenting only codon-randomized gene sequences after removing backbone portions of the plasmid vectors. For example, referring to FIG. 4, before fragmenting extracted plasmid vectors after transformation using *E. coli*, only gene regions may be selectively purified using a restriction enzyme after removing backbone portions of plasmid vectors. When sequences are confirmed by randomly fragmenting entire plasmids, approximately ⅔ of sequencing information may be backbone sequences of a plasmid. Therefore, to address this, only codon-randomized gene sequence portions may be purified in advance by cutting plasmid vectors using a restriction enzyme.

In one embodiment of the present disclosure, the sizes of the fragments may be determined within a range of 100 to 1,000 bp for easy analysis.

In step S3 Of FIG. 1, sequences of the fragmented nucleic acid fragments are confirmed.

In one embodiment of the present disclosure, the sequence validation may be performed using Sanger method or a massively parallel manner. In a desirable embodiment of the present disclosure, the sequence validation may utilize next generation sequencing (NGS). When an Illumina HiSeq 2500 platform is used as the next generation sequencing, 150 million reads with a 150 bp length may be prepared. The next generation sequencing may include, but is not limited to, methods such as Illumina, Roche 454, SOLid, Helicos, PacBio and Ion-Torrent.

In one embodiment of the present disclosure, before sequencing, connecting adaptor sequences and index sequences to terminal ends of the fragmented nucleic acid fragments may further included. The adaptor sequences and the index sequences may be used for next generation sequencing.

In step S4 of FIG. 1, the sequence-confirmed nucleic acid fragments are reassembled into original gene sequences before the fragmentation using the codon-randomized base sequences.

Referring to FIG. 5, primary sequences of each gene before the fragmentation can be recovered from sequencing information that was randomly fragmented and validated by computational analysis using an assembler program. In one embodiment of the present disclosure, the reassembling may include excluding low-quality sequence information among the base sequence-confirmed nucleic acid. In one embodiment of the present disclosure, low-quality sequence information may be cut or removed based on a Phred quality score representing reliability of each by among the sequencing information. In general next generation sequencing information, quality of sequences of both ends may be lower than middle portion sequences. Therefore, when a Phred score of sequences of both ends of nucleic acid fragments is lower than 30 (accuracy of 99.9%), information of the sequences may be removed. When a Phred score of 30 or less is present in a middle portion of the sequences, entire nucleic acid fragments may be removed. Therefore, after the step, nucleic acid fragments having a sequence accuracy of 99.9% or more would remain.

In one embodiment of the present disclosure, the reassembling may include searching mapping locations of the base sequence-confirmed nucleic acid fragments using codon-randomized base sequences and connecting nucleic acid fragments having overlapping sequences with respect to the mapped locations.

In one embodiment of the present disclosure, in the step of searching mapping locations of the nucleic acid fragments, NovoAlign may be used. NovoAlign is a program frequently used in genomic research and may be used to confirm a concordance degree between reference sequences and the sequence-confirmed nucleic acid base sequences, and mapping locations by aligning nucleic acid fragments to reference sequences. In one embodiment of the present disclosure, a mapping location of each nucleic acid fragment can be identified using codon-randomized sequences including degenerate nucleotides such as N, R, Y and the like as reference information of NovoAlign.

In one embodiment of the present disclosure, the reassembling may include resorting nucleic acid fragments having overlapping sequences among the mapped nucleic acid fragments to a small partial cluster. This step may be resorting nucleic acid fragments having overlapping sequences based on mapped locations to cluster nucleic acid fragments derived from the same codon-randomized gene sequences. When each nucleic acid fragment aligned through NovoAlign is mapped to the same location but primary codon-randomized gene sequences before fragmentation step are different, the same sequences are not shared. This means that nucleic acid fragments fragmented from primary identical codon-randomized gene sequences only share the same sequences. Therefore, when identity of sequences of portions, in which different nucleic acid fragments are overlapped based on mapped locations, is compared, all nucleic acid fragments derived from the same origin may be gathered again. In one embodiment of the present disclosure, the lengths of the overlapping sequences may be 20 to 80 bp, preferably 40 to 60 bp. For exact classification, setting an optimal length of the overlapping sequences to be compared is necessary. Extremely short lengths of the overlapping sequences are inefficient since a probability that two nucleic acid fragments derived from different codon-randomized gene sequences share the same sequences in a corresponding length by chance increases. On the other hand, when the lengths of the overlapping sequences are extremely long, nucleic acid fragments sharing short overlapping sequences may not be used and, thus, assembly depth is lowered, thereby deriving exact universal sequences would be difficult.

In one embodiment of the present disclosure, the reassembling may include deriving common major sequences based on most frequently read sequences. In one embodiment of the present disclosure, major sequences of a codon randomized gene may be derived in a manner that most frequently read sequences in one location based on reference sequences and mapping locations are determined to consensus sequences in a corresponding location. When all nucleic acid fragments are resorted to small partial clusters after the resorting, nucleic acid fragments fragmented from one codon-randomized gene sequence type only remain in one cluster. Therefore, when consensus sequences of the nucleic acid fragments are derived, primary gene sequences before fragmentation can be recovered. Although low-quality analysis information based on a Phred score of 30 is removed in a first step, some nucleic acid fragments may have sequencing errors in a probability of 1/1000. So as to correct such errors, high depth being a largest advantage of the next generation sequencing may be used. That is, most frequently read sequences in one location based on a reference and a mapped location may be determined as consensus sequences of a corresponding location. Probability that the same error is repeated with the same DNA sequence in the same position is low and, although such repetitive occurrences occur, the number of other reads not including errors are much higher in the corresponding location, error correction through the high depth is possible. Therefore, final consensus gene sequences may be derived in a manner of determining most predominant sequences per location of a gene. Through this, a codon randomized second gene library may be finally synthesized. In one embodiment of the present disclosure, an error-free gene library coding the same protein but having different base sequences manufactured according to the method is provided.

In one embodiment of the present disclosure, in the reassembled second gene library or the error free gene library, desired gene sequences may be selectively amplified.

In one embodiment of the present disclosure, for the selective amplification, barcode tag sequences may be used. Both ends of the codon randomized gene library may include the barcode tag sequences included in the first designing step and the barcode tag sequences of individual codon-randomized gene sequences exhibit independent forms. In addition, identification of gene sequences and barcode tag sequences is possible through computational analysis of the next generation sequence information. Therefore, when PCR is carried out using corresponding barcode tag sequence as annealing sites of primers, only one desired gene sequence type of an entire library may be selectively amplified.

In another embodiment of the present disclosure, for the selective amplification, barcode sequences derived from a vector may be used. While barcode tag sequences of both ends of the gene for selective recovery are not included, only one desired gene sequence type may be selectively amplified by using sequences derived from a vector in a cloning process as barcode sequences. In one embodiment of the present disclosure, the vector may be a pUCN vector. The pUCN vector is a vector library manufactured by the present inventors through modification of the pUC19 vector and may be manufactured by cloning a 102 bp novel fragment after cutting multiple cloning sites (MCS) of pUC19 using a restriction enzyme. The inserted sequences include recognition sequences of a novel restriction enzyme and may include 20 bp 'N' sequences at both ends of the recognition sequences. Therefore, when a specific nucleic acid fragment is cloned, independent barcode sequences may automatically be included, although the barcode sequences were not included in a synthesis process.

In another embodiment of the present disclosure, for the selective amplification codon, randomized sequences themselves may be used. So as to selectively amplify one gene sequence type in a gene library, all gene sequences require tag sequences functioning as different barcodes. However, since sequences of all genes of a synthesized library themselves may function as a barcode through codon-randomized, only one desired gene sequence type may be selectively amplified without a separate tag.

As the method of selectively amplifying the desired gene sequences, a conventional method of selectively recovering or amplifying specific gene sequences may be used.

In another embodiment of the present disclosure, provided is a method of synthesizing a library of mutated genes, the method comprising providing a gene library comprising randomized codons encoding to a specific protein sequence but having different nucleic acid base sequences; inducing mutagenesis of the gene library, fragmenting the mutated gene library into nucleic acid fragments, confirming base sequences of the nucleic acid fragments, and reassembling the base sequence-confirmed nucleic acid fragments into gene sequences before fragmentation using codon-randomized base sequences.

According to the same method as in step S1 of FIG. 1, a gene library including randomized codons encoding a specific protein sequence but having different nucleic acid base sequences is provided.

In step S11 of FIG. 1, mutagenesis in the gene library occurs. An advantage of Jigsaw assembly of the present disclosure is that all sequences of several hundred to thousands of gene libraries or more may be confirmed in a batch and in parallel using the next generation sequencing. Therefore, when a random mutagenesis method generally used as a conventional protein engineering method and Jigsaw assembly are combined, a novel protein engineering method that may confirm a large amount of genotypes having a desired phenotype after engineering an entire region of a target protein may be achieved.

In one embodiment of the present disclosure, the mutagenesis may be random mutagenesis. In one embodiment of the present disclosure, the mutagenesis may use mutagenesis amplification. A nonsynonymous library may be synthesized by modifying base sequences at a random location during a synthesis process of the codon-randomized gene library.

In one embodiment of the present disclosure, in the mutagenesis amplification, error prone PCR may be used. During the synthesis process of the codon-randomized gene library, error prone PCR may be performed instead of normal PCR in a PCR process after ligation.

In the same method as in step S2 of FIG. 1, the mutated gene library may be fragmented into nucleic acid fragments and, in the same manner as in step S3 of FIG. 1, sequences of the fragmented nucleic acid fragments may be confirmed.

In the same method as in step S4 of FIG. 1, a library of mutated genes may be synthesized by reassembling the base sequence-confirmed nucleic acid fragments into original gene sequences before fragmentation using codon-randomized base sequences.

In one embodiment of the present disclosure, the library of mutated genes may be a cluster of gene sequences having different base sequences encoding a protein having mutated amino acids in a specific location. In another embodiment of the present disclosure, the library of the mutated genes may be a cluster of different base sequences encoding a protein having random mutations in an entire region of the protein.

In one embodiment of the present disclosure, a library of mutated genes manufactured according to the method is provided.

In one embodiment of the present disclosure, in the library of the mutated genes, desired gene sequences may be selectively amplified. As a method of selectively amplifying desired gene sequences, the same method as disclosed above may be used.

In the present disclosure, by using a combination of different codons translated into the same protein based on protein sequences of a gene to synthesize, a nucleic acid combination library which are finally translated into same protein sequences but have a variety of nucleic acid base sequences is generated. Alternatively, due to errors occurred during synthesis, a protein sequence combination library in which some protein sequences are changed to similar protein sequences is generated.

A novel experimental method that permits quantitative research for expression and functions of the gene by using a nucleic acid base sequence combination and a similar protein sequence combination of a gene obtained as described above is provided. The codon-randomized nucleic acid base sequence library provides a novel experimental method that may measure a correlation of gene expressions according to change in a codon by changing the usage of a codon optimized to express a specific gene in vivo. For example, an expression level of a corresponding gene library may be indirectly measured by measuring the amount of GFP that is substantially simultaneously expressed after connecting a reporter gene such as a green fluorescent protein (GFP) to a downstream region of each nucleic acid base sequence combination when a gene library is synthesized.

A combination library of some similar proteins of a gene encoding a protein having mutations provides a novel experimental method of confirming that changes in some protein sequences of a specific gene influence on function of a corresponding gene. For example, since change in some protein sequences (motif) of intein as a gene involved in protein splicing has crucial effect on corresponding intein function, unknown optimized novel inteins may be discovered when the protein sequences library is used.

Hereinafter, embodiments of the present disclosure are described using examples below.

Example 1. Synthesis of Codon-Randomized kanR Gene Library

Aminoglycoside transferase gene (816 bp) generally known as a kanamycin resistance gene (kanR) imparts resistance to the antibiotic kanamycin, and is widely used as a marker gene in synthetic biology since survival of cells in a medium including kanamycin is determined depending upon presence or absence of a corresponding gene. In the current example, a codon-randomized library of a gene was synthesized using a kanR gene as a target gene.

So as to derive codon-randomized nucleic acid base sequences including degenerate nucleotides using KanR protein sequences, a program called "Codon Randomizer" was developed in the Phython programming language. This program inserts degenerate sequences such as N (Combination of A, T, C and G), R (Combination of A and G), Y (combination of T and C), etc. into codons translating a specific amino acid. Through such a method, the KanR protein sequences may be reversely translated into degenerate nucleic acid base sequences.

Oligos necessary for library synthesis were designed based on the degenerate nucleic acid base sequences. So as to use LCR method among various gene synthesis methods as an oligo assembly method, interval gaps between oligos were removed and both ends of the gene included barcode tag sequences (25 bp), restriction enzyme recognition sequences (EcoR I and Hind III) and flanking sequences (20 bp).

Oligonucleotides were classified into five sense oligonucleotides and four nonsense oligonucleotides and designed as summarized in Table 1 below. The lengths of the oligonucleotides were 125 bp to 199 bp and overlap of 99 bp was present between the sense oligonucleotides and the nonsense oligonucleotides.

TABLE 1

(GAATTC: EcoR I site, AAGCTT: Hind III site)

| | |
|---|---|
| Sense 1 (Sequence No. 1) | CACAGTACCAAACACGTGTGgaattcNNNNNCNNNNNANNN NTNNNNCNNNNNAatgtcncayatycarcgngaracntcn tgytcncgnccncgnctnAaytcnaayatggaygcngay ctntayggntayaartgggcncgngayAaygtnggncar tcnggngcnacnatytaycgnctntayggnaarccngay gcnc (199 mer) |
| Nonsense 1 (Sequence No. 2) | Tnggnagnggcatraaytcngtnagccarttnagncgna ccatytcrtCngtnacrtcrttngcnacnganccyttnc crtgyttnagraanagytCnggngcrtcnggyttnccrt anagncgrtaratngtngcnccngaytGnccnacrttrt cncgngcccayttrtanccrtanagrtcngcrtccatrt tng (198 mer) |
| Sense 2 (Sequence No. 3) | Cngarctnttyctnaarcayggnaarggntcngtngcna aygaygtnaCngaygaratggtncgnctnaaytggctna cngarttyatgccnctncCnacnatyaarcayttyatyc gnacnccngaygaygcntggctnctnaCnacngcnatyc cnggnaaracngcnttycargtnctngargartayccng ayt (198 mer) |
| Nonsense 2 (Sequence No. 4) | Gncgraanacncgrtcngarttraanggrcarttrcana cnggratngArtgnagncgncgnagraanacngcnagg crtcnacratrttytcncCngartcnggrtaytcytcna gnacytgraangcngtyttnccnggraTngcngtngtna gnagccangcrtcrtcnggngtncgratraartgyttra tng (198 mer) |
| Sense 3 (Sequence No. 5) | Cnggngaraayatygtngaygcnctngcngtnttyctnc gncgnctncAytcnatyccngtntgyaaytgyccnttya aytcngaycgngtnttycGnctngcncargcncartcnc gnatgaayaayggncntngtngaygcntCngayttygayg aygarcgnaayggntggccngtngarcargtntggaarg ara (198 mer) |
| Nonsense 3 (Sequence No. 6) | Trcanccratnagyttnccytcrtcraaratnagrttrt cnagngaraArtcnccrtgngtnacnacngarttraarc araanggnagnagyttrtGcatytcyttccanacytgyt cnacnggccanccrttncgytcrtcrtCraartcngang crtcnacnagnccrttrttcatncgngaytgngcytgng cna (198 mer) |
| Sense 4 (Sequence No. 7) | Tgcayaarctnctncnttytgyttyaaytcngtngtna cnayggngAyttytcnctngayaayctnatyttygayg arggnaarctnatyggntGyatygaygtnggncgngtng gnatygcngaycgntaycargayctngCnatyctntgga aytgyctnggngarttytcnccntcnctncaraarcgnc tnt (198 mer) |
| Nonsense 4 (Sequence No. 8) | Tcaraaraaytcrtcnagcatnagrtgraaytgnagytt rttcatrtcNggrttrtcratnccrtayttytgraanag ncgyttytgnagnganggNgaraaytcnccnagrcartt ccanagratngcnagrtcytgrtancgrtcngcratncc nacncgnccnacrtcra (173 mer) |
| Sense 5 (Sequence No. 9) | Tycaraartayggnatygayaayccngayatgaayaarc tncarttycayctnatgctngaygartttyttytgaNNNN ANNNNTNNNNCNNNNANNNNTaagcttGAGTCAGTTTCA GCTACCTG (125 mer) |

Oligonucleotides were manufactured and synthesized by Intergrated DNA Technology (IDT), USA. The synthesized oligonucleotides had an OH functional group at a 5' terminal. Therefore, for ligation, an enzyme called kinase was used to phosphorylate the OH functional group. The concentrations of all of the oligonucleotides were diluted to 100 μM using nuclease-free water and then 3 uL of each sense oligonucleotide, 6 uL of 10×PNK buffer and 3 uL of T4 PNK were mixed. Subsequently, a final reaction volume was adjusted to 60 uL by filling a remaining volume with nuclease-free water and then reaction was carried out overnight at 37° C. The nonsense oligonucleotides were also processed using the same method.

Subsequently, complementary sense oligonucleotides and nonsense oligonucleotides were annealed by elevating temperature to 95° C. and then slowly decreasing the temperature, and, in this state, gaps between the oligonucleotides were filled using a thermo-stable ligase, thereby completing templates for polymerase chain reaction (PCR). 20 uL of a pool of each of 5'-phosphorylated sense oligonucleotides and nonsense oligonucleotides was mixed, and 5 uL of 10× Ampligase buffer and 2.5 uL of Ampligase were added thereto. Subsequently, so as to adjust a total reaction volume to 50 uL, 2.5 uL of nuclease-free water was additionally added thereto, and reaction was carried out as summarized in Table 2 below.

TABLE 2

| Protocol | Temperature | Time |
| --- | --- | --- |
| Initial denaturation | 95° C. | 3 minutes |
| Annealing | 94° C. | 1 minute |
|  | 93° C. | 1 minute |
|  | \| | \| |
|  | 69° C. | 1 minute |
|  | 70° C. | 1 minute |
| Ligation | 70° C. | 2 hours |
| Storage | 4° C. | ∞ |

At first 95° C., all of the oligonucleotides are denatured into single strands and, by slowly lowering temperature, annealing of the sense oligonucleotides and the nonsense oligonucleotides having complementary sequences proceeds. Subsequently, at 70° C., gaps between oligos were connected by ligase.

Finally, using common flanking sequences of the two ends included in the design process of the oligonucleotides as primer sequences, PCR was carried out under conditions as summarized in Tables 3 and 4, thereby synthesizing a codon-randomized kanR gene library.

TABLE 3

| Nuclease-free water | Template (ligation reaction product) | 2x KAPA polymerase mix | Forward primer | Reverse primer |
| --- | --- | --- | --- | --- |
| 7 μl | 1 μl | 10 μl | 1 μl | 1 μl |

TABLE 4

| Protocol | Temperature | Time |
| --- | --- | --- |
| Initial denaturation | 95° C. | 3 minutes |
| Denaturation | 95° C. | 30 seconds |
| Annealing | 60° C. | 30 seconds |
| Elongation | 72° C. | 1 minute/1 kb |
| The above three steps were repeated 20 times | | |
| Final elongation | 72° C. | 10 minutes |
| Storage | 4° C. | ∞ |

In Table 4, the elongation time may be changed depending upon the lengths of nucleic acid fragments to be amplified (1 minute/kb). Reaction products of the PCR reaction were confirmed through gel electrophoresis and purified. FIG. 6 illustrates an agarose gel electrophoresis result of the synthesized kanR gene library and exact consensus in the synthesized size (911 bp).

Example 2. Limitation of the Number of Gene Sequences Through Cloning and Transformation In Example 1, each of the both ends of the synthesized codon-randomized kanR gene library commonly included two enzyme recognition sequence types (EcoR I and Hind III). In addition, multiple cloning sites (MCS) of pUC19 as a backbone plasmid used in the present experiment also included the same sequences. Therefore, the plasmid and the gene library were substantially simultaneously double digested using EcoR I and Hind III enzymes, and only one gene sequence type was individually inserted into one plasmid through ligation, thereby completing manufacture of a plasmid library. Referring to FIG. 7, a plasmid library manufactured as described above was transformed into *E. coli*. Since one cell probabilistically uptakes only one plasmid type, the number of codon-randomized gene sequences may be limited by limiting the number of *E. coli* cells. In the present experiment, the number of the codon-randomized gene sequences was limited to a maximum of 2000 by limiting to approximately 2000 colonies after culturing cells transformed with the library plasmid in a solid medium including ampicillin used as a marker of a pUC19 plasmid.

Example 3. Random Fragmentation and Adaptor Sequence Connection

All of the 2000 colonies limited in Example 2 were gathered and cultured in one pool, and then whole plasmids were substantially simultaneously extracted. The extracted plasmids were randomly fragmented into approximately 300 bp using an M220 Focused-Ultrasonicator™ manufactured by Covaris (USA) and then only 200 to 400 bp fragments were selectively purified through gel electrophoresis. FIG. 8 illustrates a fragmentation conditions and a gel electrophoresis result.

When DNA fragments were randomly fragmented, overhang was generated at both ends of the DNA fragments and phosphate groups, necessary in ligation, at 5' terminals are damaged. Referring to FIG. 9, so as to the damaged phosphate groups, an end repair process was carried out. 1 to 5 μl of the fragmented DNA as a starting material was mixed as summarized in Table 5 below. The volumes of the fragmented DNA and sterile water may be changed, and a total reaction volume was adjusted to 100 μl. Subsequently, reaction was carried out for 30 minutes at 20° C. and then only DNA was purified.

TABLE 5

| Fragmented DNA | 1~5 μl |
| --- | --- |
| NEB next end repair reaction buffer (10x) | 10 μl |
| NEB next end repair enzyme mix | 5 μl |
| Sterile water | Changeable |
| Total volume | 100 μl |

In addition, adaptor loops necessary in Illumina sequencing being next generation sequencing were connected through dA tailing and adaptor ligation. 1 to 5 μl of end repaired DNA as a starting material was mixed as summarized in Table 6 below. The volumes of the end repaired DNA and sterile water may be changed and the total reaction volume thereof was adjusted to 50 μl. Subsequently, reaction was carried out for 30 minutes at 37° C. and then only DNA was purified.

TABLE 6

| End repaired DNA | 1~5 μl |
| --- | --- |
| NEB next dA tailing reaction buffer (10x) | 5 μl |

TABLE 6-continued

| Klenow fragment (3'→5' exo-) | 3 μl |
| Sterile water | Changeable |
| Total volume | 50 μl |

Subsequently, loop cutting through a user enzyme and index sequence connection through PCR were carried out. DNA, in which dA tailing was completed, as a starting material was mixed as summarized in Table 7 below. Subsequently, reaction was carried out for 15 minutes at 20° C., and 3 ul of a user enzyme mix was added thereto and well mixed. Subsequently, reaction was further carried out for 15 minutes at 37° C. When the reaction was terminated, only DNA was purified.

TABLE 7

| dA tailed DNA | 10 μl |
| Quick ligation reaction buffer (2×) | 25 μl |
| NEB next adaptor (15 μM) | 10 μl |
| Quick T4 DNA ligase | 5 μl |
| Total volume | 50 μl |

DNA in which adaptor ligation was completed was mixed as summarized in Table 8 below and PCR was carried out under conditions summarized in Table 9 below. When the reaction was terminated, only DNA was purified.

TABLE 8

| Adaptor-ligated DNA | 20 μl |
| Universal PCR primer (25 μM) | 2.5 μl |
| Index primer (25 μM) | 2.5 μl |
| 2x KAPA Hifi polymerase mix | 25 μl |
| Total volume | 50 μl |

TABLE 9

| Protocol | Temperature | Time |
| --- | --- | --- |
| Initial denaturation | 98° C. | 30 seconds |
| Denaturation | 98° C. | 10 seconds |
| Annealing | 60° C. | 30 seconds |
| Elongation | 72° C. | 30 seconds |
| The above three steps were repeated 8 times | | |
| Final elongation | 72° C. | 5 minutes |
| Storage | 4° C. | ∞ |

Through the reactions, the plasmid pool cloned with the gene library was resultingly fragmented into 200 to 400 bp nucleic acid fragments and, thus, preparation for Illumina sequencing was completed. Sequences of a corresponding sample was analyzed using an Illumina Hiseq 2500 platform in which 150 million reads having a length of 150 bp may be prepared in a batch.

Example 4. Reassembly to Gene Sequences Before Fragmentation

So as to recover gene sequences before primary fragmentation using next generation sequencing information through random fragmentation and sequence validation in Example 3, an assembler program using a Phython programming language was developed. Using the program, computational analysis of next generation sequencing information (NGS data) was carried out. A corresponding program was fundamentally based on an overlap based sequence reassembly concept and largely composed of four steps as follows.

(1) Exclusion of Low-Quality Reads Through Quality Score

Based on a Phred quality score 30 (accuracy is 99.9%), nucleic acid fragments were cut when Phred quality scores of both ends of the nucleic acid fragments were lower than 30, and, when Phred scores of the middle portions of nucleic acid fragments are 30 or less, entire reads were removed. Therefore, after performing the process, only reads having a base sequence analysis accuracy of 99.9% or more remained.

(2) NovoAlign

In the present research, so as to search a mapping location of each nucleic acid fragment, codon-randomized gene sequences including degenerate sequences such as N, R, Y, etc. were used as reference information of NovoAlign.

(3) Small Classification of Nucleic Acid Fragments Through Sequence Identity Comparison All nucleic acid fragments derived from the same origin, namely, the same codon-randomized gene sequences were collected again by comparing identity of sequences of portions, in which different reads overlap, based on a mapped location. Nucleic acid fragments having overlapping sequences were re-classified to clusters of nucleic acid fragments derived from the same codon-randomized gene sequences. Since all nucleic acid fragments were reclassified to small partial clusters, one cluster had nucleic acid fragments fragmented from one codon-randomized gene sequence type.

(4) Drawing of Consensus Sequences from Small Classified Nucleic Acid Fragments

Figure 10:
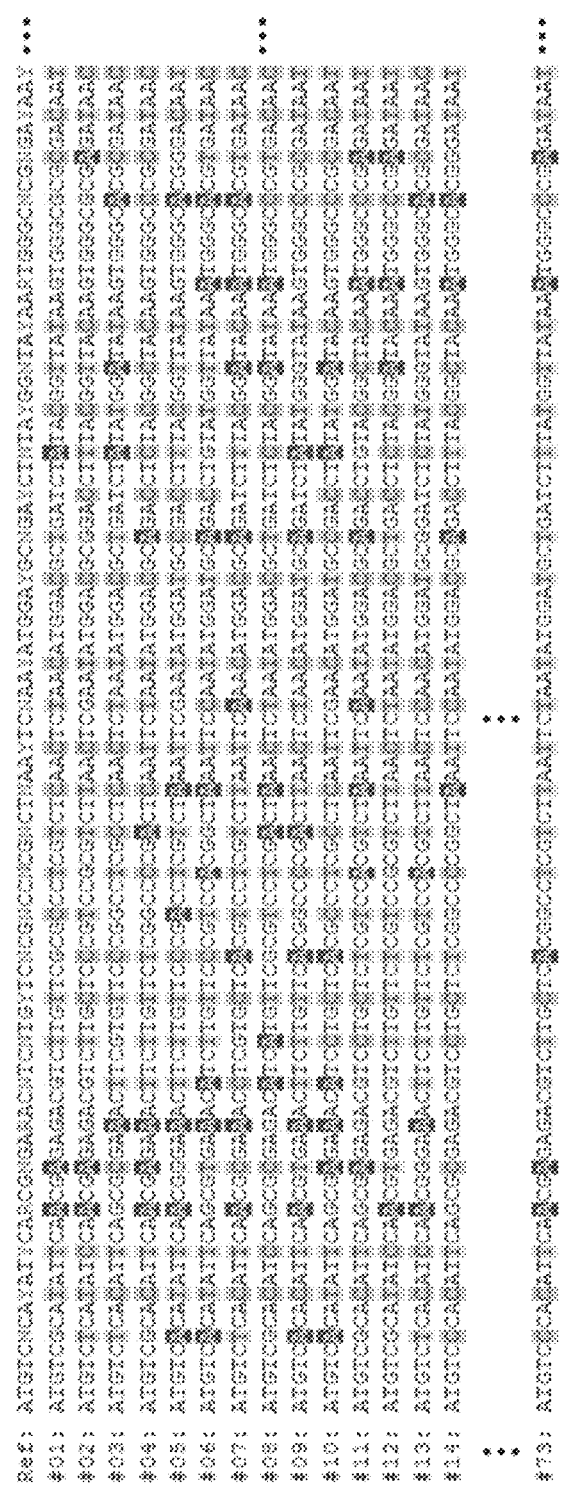

Based on a reference and a mapped location, a sequence most frequently read in one location was determined as a consensus sequence of a corresponding location. In a manner of determining, one by one, a most predominant nucleotide per location of a gene, final consensus gene sequences were derived. Accordingly, reassembling the sequence validated nucleic acid fragments into gene sequences before fragmentation was successfully performed. As a result, 73 error-free gene sequences were identified and it was confirmed that all of the gene sequences were a codon-variant library type having a variety of different codon combinations. An analysis result for a kanR gene library is illustrated in FIG. 10. In FIG. 10, a first line (Ref) illustrates codon-randomized sequences derived from a KanR protein, and a second line and the other lines illustrate 73 error-free sequences of the kanR gene reassembled through computational analysis.

Example 5. Selective Recovery Using Barcode Tag

Each of both ends of the kanR gene library includes 25 bp barcode tag sequences included in the primary design process. By performing amplification through PCR using the barcode tag sequences as an annealing site of a primer, only one desired gene sequence type of an entire whole library was selectively amplified. Among 73 error-free sequences reassembled in Example 4, PCR for 28 sequences was independently carried out. Table 10 below shows sequences of primers used in the experiment and annealing temperatures (Tm) in PCR.

TABLE 10

| # | Forward primer sequences | Reverse primer sequences | Tm (° C.) |
|---|---|---|---|
| 1 | ATATCGCGGACACGTACCTCG CAGA (Sequence No. 10) | AATCTTCGACGGTGGACCGTT GTTG (Sequence No. 11) | 65 |
| 2 | ATGGCGTAAAGGCATGTCACT TTCA (Sequence No. 12) | ACGCCTACCTGCTCCAGCTAT CGGC (Sequence No. 13) | 65 |
| 3 | ATTCCACTTATGTGTATAACCA CAA (Sequence No. 14) | ATCACTCTACGGTCGAGAGCT CGCA (Sequence No. 15) | 65 |
| 4 | ATTGCCTGTAGTGTTATTACTT AGA (Sequence No. 16) | ATAACTCAGAGGAGAATCTGT ACGA (Sequence No. 17) | 65 |
| 5 | ATTTCGGTCAGATTTATCCCAC TAA (Sequence No. 18) | AATCCTTGGAGTCCCACCCAT TGCT (Sequence No. 19) | 65 |
| 6 | CAAACAGCAAATGTTCTTCCTG AAA (Sequence No. 20) | AAAACTGCACGACGCACCAGT TTAG (Sequence No. 21) | 65 |
| 7 | CAATCAGATAGAGATCTTACA TGAA (Sequence No. 22) | ATCGATATCTGCAACAAACAT TTAG (Sequence No. 23) | 65 |
| 8 | CACGCTCCTATAACTTCATCTA GTA (Sequence No. 24) | ACCCGTTCTAGCCGGATTCTT AAAT (Sequence No. 25) | 65 |
| 9 | CAGACTCTTATCTCTTTAACCG CTA (Sequence No. 26) | ACATCTGTAGGGATAATCGGT CCCC (Sequence No. 27) | 65 |
| 10 | CATCCTAACAGGGGTTCTCCGT TAA (Sequence No. 28) | AAGCGTCCACGTAAGAGACTT GGTC (Sequence No. 29) | 65 |
| 11 | CCCACATTTACAGCTTCTTCGG TTA (Sequence No. 30) | ATGCTTAACGGGGTTATAAAT TTCA (Sequence No. 31) | 65 |
| 12 | CTGCCTATGACTGGTGTCCCTG ATA (Sequence No. 32) | ATACTTTATCGCTAGACCAAT TAAC (Sequence No. 33) | 65 |
| 13 | GAATCTTAGAAAATTGATACG ATGA (Sequence No. 34) | ATAAATTACTGAAAGAACTCT CTTA (Sequence No. 35) | 60 |
| 14 | GAATCTTGAAATCATTTAACAA TGA (Sequence No. 36) | ACGCATTGCCGCCACAAGGAT TCGT (Sequence No. 37) | 65 |
| 15 | GACGCATTGACTACTTTGTCTT GGA (Sequence No. 38) | ACCGCTTTGAGTTCTATTTTTG GCA (Sequence No. 39) | 65 |
| 16 | AATACTTTAATTCTTATGTCTA TTA (Sequence No. 40) | ATACATCTTGGTCCTAGTCAT CATG (Sequence No. 41) | 58 |
| 17 | AATTCCACAAATAGTTAATCG ATTA (Sequence No. 42) | ATTGTTCGATGGCATAAAGGT GCCT (Sequence No. 43) | 58 |
| 18 | AATTCCTGAAGTGTTTCAGCTT TAA (Sequence No. 44) | ACTAATCGCAGATGGATGTCT CAAC (Sequence No. 45) | 65 |
| 19 | AATTCGTTAACATATAAGTCTT TGA (Sequence No. 46) | ACACGTCAACGTCATACGCCT ACTC (Sequence No. 47) | 61.75 |
| 20 | AGATCGCCAATTGATCTTTCTA GGA (Sequence No. 48) | ATGACTACCAGGTCTATCCCT CAGA (Sequence No. 49) | 65 |
| 21 | AGGACAACCACTTTTCAAGCA GCAA (Sequence No. 50) | ACCGATGTACGGCCCACGTCT CGCT (Sequence No. 51) | 65 |
| 22 | GACTCTTCTAGGTTTTCTTCTTT CA (Sequence No. 52) | AATCTTGGGCGCATGACCCTT CCGT (Sequence No. 53) | 65 |
| 23 | GATGCTGGGACACGTTACCCTT AGA (Sequence No. 54) | AGCCATTGTTGAGCTATGCAT CACG (Sequence No. 55) | 65 |
| 24 | GCCGCGTAAAAGGCTTATCCA GACA (Sequence No. 56) | ACCCCTGGGAGCGCCAACTCT TAAC (Sequence No. 57) | 65 |
| 25 | GGAGCTGTTACATTTTTAACTT CAA (Sequence No. 58) | ACACGTAACAGTTCCACACCT GGCT (Sequence No. 59) | 65 |
| 26 | GGAGCTGTTACATTTTTAACTT CAA (Sequence No. 60) | AAAACTCTTTGCGCCACACAT CTCG (Sequence No. 61) | 65 |

TABLE 10-continued

| # | Forward primer sequences | Reverse primer sequences | Tm (° C.) |
|---|---|---|---|
| 27 | GGCCCCGTCAAGCATGCGTCTT ATA (Sequence No. 62) | AGAAGTAATTGCTGGACGTCT GCAA (Sequence No. 63) | 65 |
| 28 | GGCTCTAGAATAATTTGATCG ATAA (Sequence No. 64) | ACCCGTAATGGGCTGAAACGT CGCG (Sequence No. 65) | 65 |

Through PCR, all of the 28 gene sequences were successfully amplified and, when the gene sequences through Sanger sequencing and the gene sequences recovered through computational analysis of the next generation sequencing were compared, all 28 gene sequences were 100% matched. These results are illustrated in FIG. 11. This proves accuracy of Jigsaw assembly.

Example 6. Synthesis and Analysis of Codon-Randomized tolC Gene Library

A tolC (1482 bp) gene used in Example 6 is a gene encoding a TolC protein as an outer membrane protein. Since the TolC protein is involved in secretion of hemolysin, introduction of a protein, release of an antibiotic, etc. by reacting with an inner-membrane pump or a translocase, the tolC gene is one of marker genes used in synthetic biology. In particular, since negative selection by Colicin E1 and positive selection by sodium dodecyl sulfate (SDS) are possible using the tolC gene, unlike general antibiotic resistance genes, utilization of the tolC gene receives more attention. According to the same method as in Example 1, a codon-randomized tolC gene library was manufactured.

The pUCN vector used in Example 6 to clone the codon-randomized tolC gene library is a vector library manufactured by the present inventors through modification of the pUC19 vector. Referring to FIG. 12, MCS of pUC19 was cut using restriction enzymes, EcoR I and Pst I, and then 102 bp novel nucleic acid fragments were manufactured through cloning. The inserted nucleic acid fragment sequences include recognition sequences of Bgl II and Not I as novel restriction enzymes, and each of both ends of the recognition sequences include 20 bp 'N' sequences. Thus, when a specific DNA fragment is cloned, the specific DNA fragment has automatically independent barcode sequences although not included during synthesis. Inserted sequences are as follows: '5-GAATTCCCT-GNNNNNNNNNNNNNNNNNNNNNcagcagCTGAAGA-GATCTggatccGC GGCCGCCTTCAGctgct-gNNNNNNNNNNNNNNNNNNNNTTCTGCAG-3' (Sequence No. 66). The codon-randomized tolC gene library was cloned into the pUCN plasmid vector using the same method as in Example 2 and transformed into E. coli.

Before fragmenting the vector pool transformed using E. coli and then extracting, a backbone portion of the vector was removed using a restriction enzyme and then only a gene region was selectively purified. EcoR I and Pst I sites of the pUCN plasmid were cut using restriction enzymes and only codon-randomized gene sequence portions were purified.

Subsequently, sequence validation and reassembly processes were performed in the same manner as in Examples 3 and 4, and, as a result, 17 error-free codon-randomized tolC gene sequences were selected from the total of 1000 colonies. A result of tolC gene library synthesis is illustrated in FIG. 13.

Example 7. Evaluation of Accuracy and Efficiency of Jigsaw Assembly Through Npu Gene Library Synthesis In the present example, a gene library was synthesized using error prone PCR as a representative random mutagenesis method and then the synthesized gene library was analyzed thorough the next generation sequencing. As a target gene, Npu-pcc73102-DnaE (Npu), produced by *nostoc punctiforme*, known as having most excellent function among presently known inteins was selected. The Npu gene is a gene involved in splicing of an intein protein and is used in various fields such as chemistry, biology, biotechnology, etc.

First, to investigate possibility of protein engineering by Jigsaw assembly and to more exactly evaluate efficiency of Jigsaw assembly, a pilot study was performed.

First, degenerate amino acid sequences were derived using protein sequences of Npu using the same method as in Example 1. Referring to FIG. 14A, C terminal extein +1, +2 and +3 residues, known as critically impacting on function of intein, were included, a highly conserved +1 residue was fixed with cysteine, and 'NNN' sequences were inserted into +2 and +3 residues such that all of 20 amino acid types may be translated. Each of both ends of the degenerate amino acid sequences were elongated with a split kanR gene of approximately 20 bp. This enables selection of functional phenotypes of intein using kanamycin and, when the inserted intein has activity, the KanR protein is spliced, whereby survival in a medium including kanamycin is possible. Synthesis of the codon-randomized library was carried out in the same manner as in Example 1.

As a vector to clone the codon-randomized intein gene library, pBR322-du1 was used. This vector was manufactured by applying an intein selection system using kanR published by Muir group in 2009 to a pBR322 vector. Since a kanR gene split into 87 bp junk sequences ('TACAAATC-CGCCTAGAGCGGATTTGAACGTTGCT-GAAGCAACGGCCCGGAGG GTGGCCAGGACGGC-CATTGACTGCCAGGAATTAAC' (Sequence No. 67)) that does not function was inserted into the pBR322-du1, a KanR protein may be produced when the junk sequences are substituted with intein. Cloning was carried out using a corresponding vector using the same method as in Example 2, and transformation was carried out using E. coli. Subsequently, all nonfunctional phenotypes, which did not have activity, were removed by culturing in a medium including kanamycin.

Next, referring to FIG. 14B, when 96 colonies were selected and Sanger sequencing therefor was carried out, 95 unique gene sequences were resultingly detected. The 95 sequence-validated colonies were collected into one tube and then plasmids were extracted. Referring to FIG. 14C, the other processes were carried out in the same manner as in Example 3 and next generation sequencing using the Illumina Hiseq 2500 platform was carried out.

Figure 15:
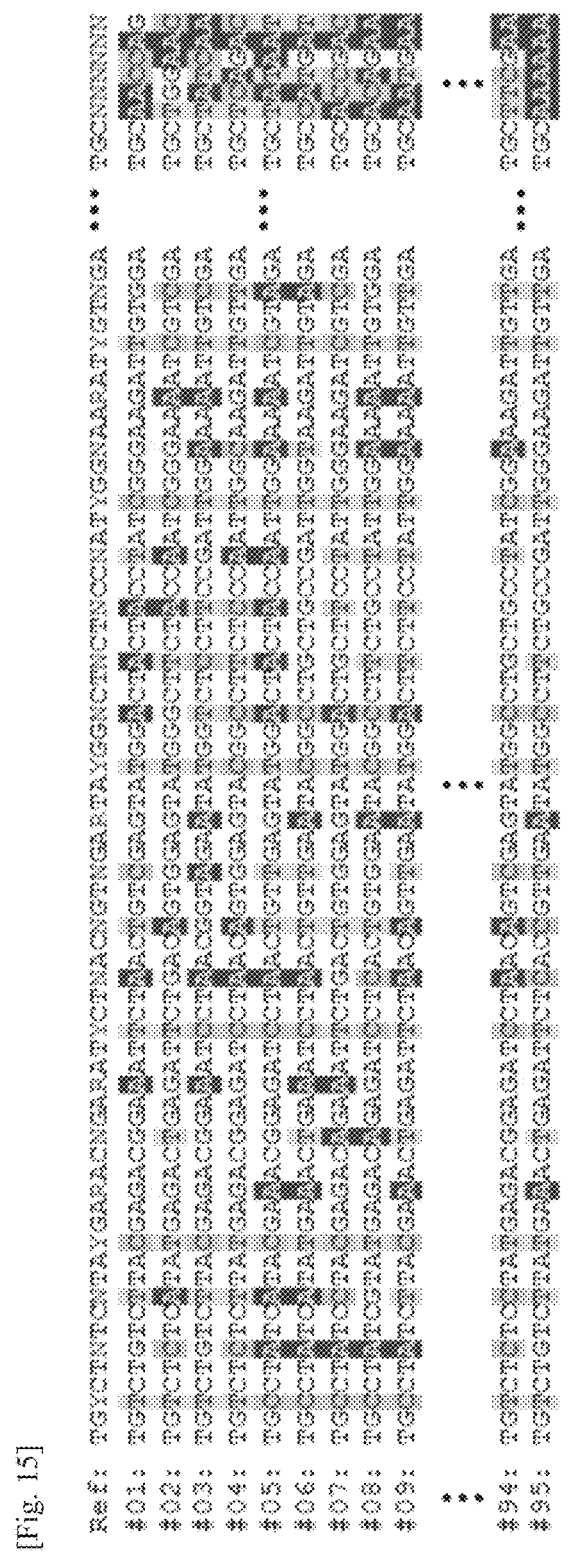

The next generation sequencing information was reassembled through the same computational analysis as Example 4, and then a result thereof was compared with the Sanger sequencing result. Results are illustrated in FIG. 15. As a result, it can be reconfirmed that all of the 95 gene sequences are 100% identical, thereby reconfirming accuracy of Jigsaw assembly.

Example 8. Test to Set Optimal Overlap Length

A simulation was carried out to investigate the amount of sequence information necessary for more efficient computational analysis, and an ideal overlap sequence length (bp) in a reassembly process.

The simulation was carried out in a manner that the number of genes reassembled under each condition and accuracy thereof were compared, randomly reducing the amount of analyzed information obtained through the primary next generation sequencing to ½, ¼, ⅛, ¹⁄₁₆ and ¹⁄₃₂, and changing the overlap length from 20 bp to 140 bp in a 20 bp unit interval.

Referring to FIG. 16, it can be confirmed that approximately 99% of an entire size of necessary data may be recovered at approximately 100× depth or more based on NovoAlign data, and an optimal overlap length is approximately 40 bp. In addition, it can be confirmed that an actual assembly depth is approximately 70% lower than a sequencing depth. This provides the basis to predict an entire size through the assembly depth in a subsequent experiment when an exact size of library is not known.

Example 9. Nonsynonymous Library Synthesis of Npu Protein Using Jigsaw Assembly and Random Mutagenesis Oligonucleotides of Npu gene were designed in the same manner as in the pilot study of Example 7, and last nonsense oligonucleotides further included oligonucleotides fixed with +1 residues (cysteine (TGC) and serine (TCG)), thereby synthesizing two libraries. Sequences of the oligonucleotides are summarized in Table 11 below.

TABLE 11

(ATGCAT: Nsi 1 site, CCATGG: Nco 1 site)

| | |
|---|---|
| Sense 1 (Sequence No. 68) | Aaagaaatgcataaactttttgccattctgyctntcntay garacngaraTyctnacngtngartayggnctnctnccn atyggnaaratygtngaraaRcgnatygartgyacngtn tcngtngayaayaayggnaayatytayacncarccngtn cncartggcaygaycgnggngarcarga |
| Nonsense 1 (Sequence No. 69) | Rtcratnggnagcatytgnccrtcnacngtcatraaytt rtgrtcyttnGtngcncgratnagnganccrtcytcnag rcartaytcraanacytcytGytcnccncgrtcrtgcca ytgngcnacnggytgngtrtaratrttnccrttrttrtc gartanacngtrcaytcratncgyttyt |
| Sense 2 (Sequence No. 70) | Rgtnttygartaytgyctngargayggntcnctnatycg ngcnacnaarGaycayaarttyatgacngtngayggnca ratgctnccnatygaygaraTyttygarcgngarctnga yctnatgcgngtngayaayctnccnaayatyaaratygc cgnaartayctnggnaarcaraaygtnt |
| Nonsense 2-1 (Cys) (Sequence No. 71) | aaatcaccatgGgtgactActgaNNNNNNGCArttngan gcratraanccrttyttnagngcraarttrtgrtcncgy tcnacnccratrtcrtanacrttytgyttnccnagrtay cgngtngcratyttratrttnggnagrttrtcnacncgc tnagrtcnagytcncgytcraaratytc |

TABLE 11-continued (ATGCAT: Nsi 1 site, CCATGG: Nco 1 site)

| | |
|---|---|
| Nonsense 2-2 (Ser) (Sequence No. 72) | aaatcaccatgGgtgactActgaNNNNNNCGArttngan gcratraanccrttyttnagngcraarttrtgrtcncgy tcnacnccratrtcrtanacrttytgyttnccnagrtay cgngtngcratyttratrttnggnagrttrtcnacncgc tnagrtcnagytcncgytcraaratytc |

Synthesis was carried out similarly to the pilot study of Example 7, and error-prone PCR instead of normal PCR was carried out to modify amino acids at random locations in a PCR process after ligation, thereby synthesizing two nonsynonymous gene library types. For convenience, a library including a C-terminal extein +1 residue fixed with cysteine (Cys) was called a CysErr pool, and a library including a C-terminal extein +1 residue fixed with serine (Ser) was called a SerErr pool.

In this regard, the term "Err" means error prone PCR and corresponds to normal PCR called "Nor".

The two synthesized codon-randomized Npu gene library types were cloned into pBR322-du1 vectors in the same manner as in Example 7 and transformed into E. coli. Subsequently, before selecting with kanamycin, the number of base populations including nonfunctional phenotypes was limited to approximately three hundred million by culturing in a solid medium including only ampicillin.

Subsequently, phenotype change was confirmed according to increase of selection pressure by culturing the same population in five media having different kanamycin concentrations (0 µM, 100 µM, 250 µM, 500 µM and 1000 µM). For convenience, a title of each pool was named as CysErr100 or the like. The "Cys" means an extein +1 residue, the "Err" means error prone PCR, the "100" means kanamycin concentration used for selection.

Subsequent processes were carried out in the same methods as in Examples 3 and 4.

Example 10. Analysis of Reassembled Npu Mutation Library

The number of the Npu codon-randomized gene sequences reassembled through Example 9 was 2,393. Thereamong, 424 sequences did not include modified amino acids and 1969 sequences included one or more modified amino acids. In the SerErr1000 pool, reassembled gene sequences were absent. Referring to FIG. 17, it can be anticipated that, in the cases of other seven pools except for CysErr0 (5×) and SerErr0 (8×) calculated as relatively low depth, CysErr100 representing a depth of 32× includes 96% or more of the total library and the other six pools include 99% or more of the total library.

In addition, when the number of gene sequences reassembled in each pool and genotypes thereof are compared each other, it can be confirmed that the number of phenotypes enduring pressure decreases as kanamycin concentration increases. In addition, genotypes of phenotypes enduring high concentration are mostly observed in low-concentration pools. Through this, it can be confirmed that all colonies under all conditions are derived from the same base population and genotypes having excellent activity are significantly present in the colonies.

So as to confirm which difference in Npu variant genotypes causes different activity based on such results, several in-depth analyses were carried out. Through such analysis, several interesting facts were confirmed.

First, it was discovered that several locations of Npu intein cannot be mutated to any amino acids. FIG. 18 illustrates presence or absence of mutation in a location of intein under each concentration condition. In the figure, a horizontal axis represents a location of the intein protein and a vertical axis represents the concentration of kanamycin used for selection.

In all pools of CysErr and SerErr, various amino acid mutations in all locations were observed in a concentration of 0 μM in which selection pressure was absent and non-functional phenotypes were included, but no variant was observed in locations 1, 2, 19, 30, 42, 81, 118~120, 126, 132, 136 and 137 under a concentration of 100 μM or more. 73.7% of these locations exists on splicing motifs (A: 1 and 2, B: 68 and 72, F: 118, 119, 120 and 126, and G: 132, 136 and 137) known as having important influence on function of intein, whereby it may be considered that the locations are key residues to maintain splicing function of Npu intein. In particular, Nos. 1 and 2 as first locations of the intein protein and No. 137 as a last location represent relatively high error ratios in the base population (CysErr0 and SerErr0) and, when selection pressure is provided, error ratios thereof are rapidly decreased to 0%, whereby it can be confirmed that N terminal and C terminal residues have more important influence on function of intein. In addition, in the case of G block, the length of the G block was shorter than other motifs, but it was observed that 42.9% of entire regions was conserved. A conservation ratio with respect to a motif length was as follows: A: 15.4%, B: 14.3%, F: 28.6% and G: 42.9%. This may be explained by a fact that the G block is highly related to nucleophilic attack due to an extein +1 residue as a first step of a splicing process of intein.

Second, it can be confirmed that amino acid mutation in the intein and the extein regions may cause functional improvement, but such functional improvement is more independent upon extein residues. Such facts were confirmed through a trend test for amino acid mutation in all regions according to increase of kanamycin pressure. Referring to FIG. 19, so as to confirm whether mutation to a specific amino acid in a specific location is preferred according to increase of kanamycin stress in an entire region including the intein regions and extein +1, +2 and +3 residues, Cochran-Armitage testing was carried out. By applying Bonferroni correction (n=20, alpha=0.05/20), it was confirmed that 16 mutations in the CysErr pool and 14 mutations in the SerErr pool were preferred. Subsequently, the genotypes of CysErr1000 and SerErr500 pool that endured highest pressure were focused.

Figure 21:
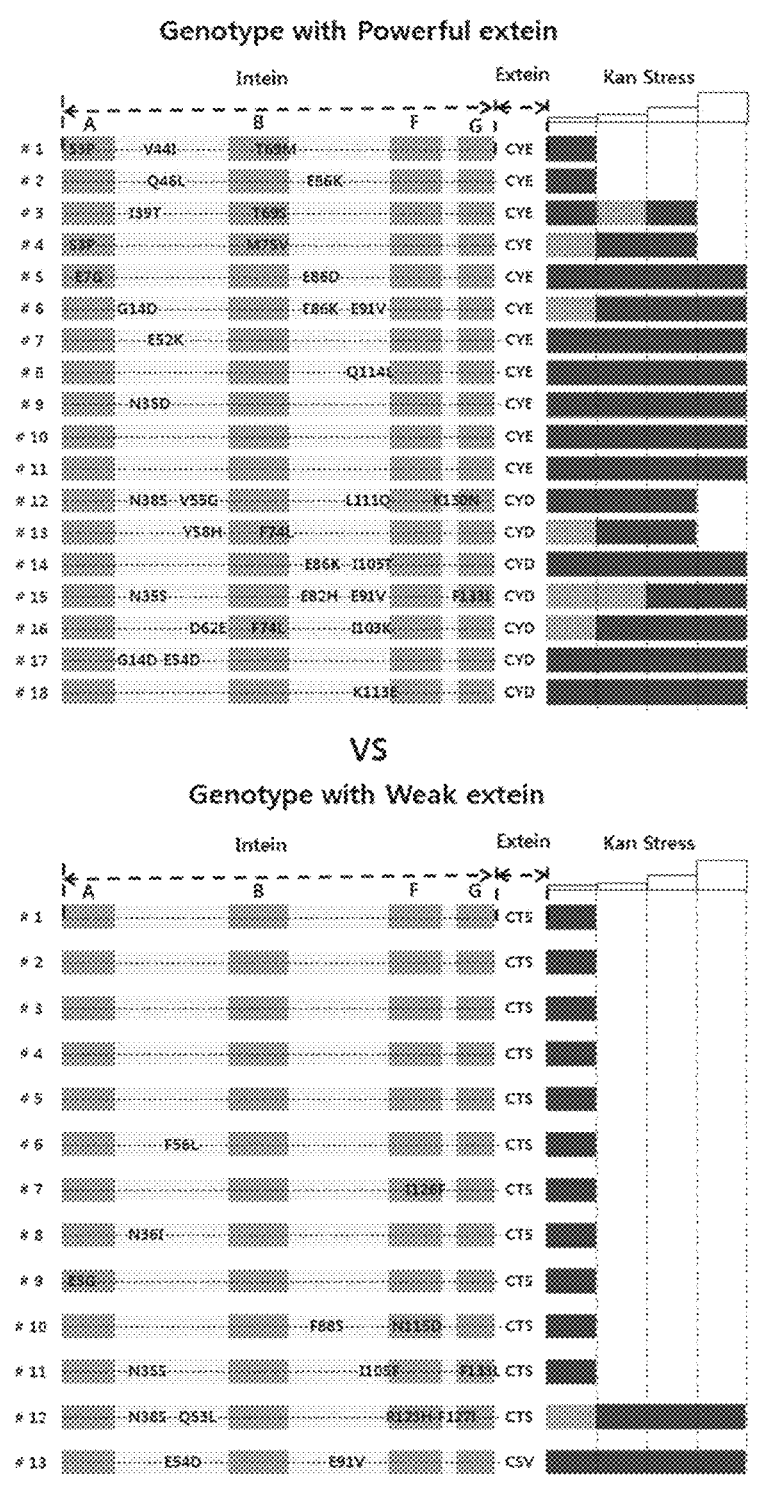

First, referring to genotypes of a CysErr1000 pool of FIG. 20, it can be confirmed that mutation to glutamic acid (Glu) or aspartic acid (Asp) of extein +3 residues, as most preferred mutations in the trend test, occupies approximately 95% of entire mutations (Glu: 19 of 34 mutations (48.7%), Asp: 18 of 34 mutations (46.2%), Ser: one mutation, and val: one mutation). Accordingly, distribution according to concentrations of mutants having CYD/CYE, which appeared to be most preferred as extein, and mutants having CTS/CSV as extein, which were not preferred but endured the highest pressure, was observed. As a result, referring to FIG. 21, most of the mutants having CYD/CYE as extein withstood kanamycin stress of 100 μM to 1000 μM largely regardless of mutation types generated within the intein and locations of the mutation types, but, among the mutants having CTS/CSV, mutants having specific mutation under a pressure of 100 μM or more only survived to a last concentration. In particular, although wild-type Npu intein, not having mutation, among the mutants having CTS was present, genotypes that endured the last concentration were mutants having N38S, Q53L, R123H and F127I. Thereamong, R123H is a fourthly preferred mutation among mutations generated in the intein region, according to the trend test. In addition, in cases of the mutants having CSV, wild-type Npu was not observed and one mutant having E54D and E91V that finally survived. E54D and E91V were firstly and secondly preferred mutations, respectively, among the intein region, according to the trend test.

SerErr pool also showed a similar trend. 77.8% of 18 mutants confirmed in SerErr500 included one or more mutations of 140D, 139F, 139M and 139Y preferred in extein mutation through the trend test, and the other 22.2% was extremely dependent upon mutation generated within the intein.

So as to more independently investigate influence of C-extein and influence of mutation within intein, a synonymous library, in which only C-extein region was mutated through normal PCR instead of error prone PCR, was synthesized again. Subsequently, kanamycin concentrations of 100 μM and 500 μM were selected and CysNor100 and CysNor500 pools were additionally analyzed. Referring to FIG. 22, when the analyzed results are compared with the C-extein region of the CysErr pool, preferences for the C-extein residues was similar. In addition, wild-type Npu having CTS was only observed in a concentration of 100 μM and wild-type Npu having CSV was not observed.

Such results may support that all of the mutations generated in the C-extein and the intein cause functional improvement of intein, but such improvement is more significant in C-extein.

Example 11. Selective Recovery Test Using Codon-Randomized Sequences Themselves

It was proven that, when a gene library was synthesized through codon randomization, selective recovery using randomized sequences themselves was possible without insertion of separate tag sequences like synthesis of the kanR gene library and the tolC gene library. In Example 10, 28 gene sequences in the CysNor100 pool were randomly selected and amplified through PCR using 30 bp of each of both ends of the codon-randomized region as primers. Subsequently, the reaction products were confirmed through Sanger sequencing. As a result, it was confirmed that only desired sequences may be exactly selectively amplified in all 28 mutations. Results are illustrated in FIG. 23.

Although the preferred embodiments of the present disclosure have been disclosed for illustrative purposes, those skilled in the art will appreciate that various modifications, additions and substitutions are possible, without departing from the scope and spirit of the invention as disclosed in the accompanying claims.

The invention claimed is:

1. A method of synthesizing a second gene library, the method comprising: providing a first gene library comprising randomized codons encoding to a specific protein sequence but having different nucleic acid base sequences; fragmenting the first gene library into nucleic acid fragments; confirming base sequences of the nucleic acid fragments; and reassembling the base sequence-confirmed nucleic acid fragments into gene sequences before fragmentation using the codon-randomized base sequences.

2. The method according to claim 1, wherein, in the providing, the randomized codons are prepared by combining different nucleic acid base sequences coding the same protein by inserting degenerate codons into gene sequences coding a specific protein sequence.

3. The method according to claim 1, wherein, in the providing, both ends of gene sequences of randomized codons in the first gene library are provided with at least one selected from the group consisting of barcode tag sequences, restriction enzyme recognition sequences and flanking sequences.

4. The method according to claim 1, further comprising controlling the number of codon-randomized gene sequences in the first gene library to a verifiable number through next generation sequencing after the providing.

5. The method according to claim 1, wherein, in the confirming, the sequence confirmation is performed using a next generation sequencing.

6. The method according to claim 1, wherein the reassembling comprises: finding mapping locations of the base sequence-confirmed nucleic acid fragments using the codon-randomized base sequences; and connecting the nucleic acid fragments having overlapping base sequences with respect to the mapped locations.

7. The method according to claim 6, wherein, in the connecting, lengths of the overlapping sequences are 20 to 80 bp.

8. A gene library prepared by the method of claim 1, wherein the gene library is the gene library without sequencing errors produced by using an assembly depth such that the gene sequence has a recovery rate of 99.9% or more based on the gene sequence before the fragmentation.

9. A method of synthesizing a library of mutated genes, the method comprising: providing a gene library comprising randomized codons encoding to a specific protein sequence but having different nucleic acid base sequences; inducing mutagenesis of the gene library; fragmenting the mutated gene library into nucleic acid fragments; confirming base sequences of the nucleic acid fragments; and reassembling the base sequence-confirmed nucleic acid fragments into gene sequences before fragmentation using codon-randomized base sequences.

10. The method according to claim 9, wherein, in the inducing, the mutagenesis is random mutagenesis.

11. The method according to claim 9, wherein, in the inducing, the mutagenesis is performed by mutagenesis amplification.

12. The method according to claim 11, wherein the mutagenesis amplification is error prone PCR.

13. The method according to claim 9, wherein the library of the mutated genes is a cluster of different base sequences encoding a protein having a mutated amino acid in a specific location.

14. The method according to claim 9, wherein, the library of the mutated genes is a cluster of different base sequences encoding a protein having random mutations in an entire amino acid region.

* * * * *

SEQUENCE LISTING

<160> NUMBER OF SEQ ID NOS: 72

<210> SEQ ID NO 1
<211> LENGTH: 199
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (32)..(35)
<223> OTHER INFORMATION: n is a, c, g, or t
<220> FEATURE:
<221> NAME/KEY: misc_feature
<222> LOCATION: (37)..(40)
<223> OTHER INFORMATION: n is a, c, g, or t
<220> FEATURE:
<221> NAME/KEY: misc_feature
<222> LOCATION: (42)..(45)
<223> OTHER INFORMATION: n is a, c, g, or t
<220> FEATURE:
<221> NAME/KEY: misc_feature
<222> LOCATION: (47)..(50)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature

```
<222> LOCATION: (126)..(126)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 1
cacagtacca aacacgtgtg gaattcnnnn cnnnnannnn tnnnncnnnn aatgtcncay      60
atycarcgng aracntcntg ytcncgnccn cgnctnaayt cnaayatgga ygcngayctn     120
tayggntaya artgggcncg ngayaaygtn ggncartcng gngcnacnat ytaycgnctn     180
tayggnaarc cngaygcnc                                                 199

<210> SEQ ID NO 2
<211> LENGTH: 198
<212> TYPE: DNA
<213> ORGANISM: Artificial Sequence
<220> FEATURE:
<223> OTHER INFORMATION: nonsense oligonucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
```

```
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
```

<222> LOCATION: (119)..(119)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 2
tnggnagngg catraaytcn gtnagccart tnagncgnac catytcrtcn gtnacrtcrt      60
tngcnacnga nccyttnccr tgyttnagra anagytcngg ngcrtcnggy ttnccrtana     120
gncgrtarat ngtngcnccn gaytgnccna crttrtcncg ngcccayttr tanccrtana    180
grtcngcrtc catrttng                                                   198

<210> SEQ ID NO 3
<211> LENGTH: 198
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)

```
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
```

<222> LOCATION: (125)..(125)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 3
cngarctntt yctnaarcay ggnaarggnt cngtngcnaa ygaygtnacn gaygaratgg     60
tncgnctnaa ytggctnacn garttyatgc cnctnccnac natyaarcay ttyatycgna    120
cnccngayga ygcntggctn ctnacnacng cnatyccngg naaracngcn ttycargtnc    180
tngargarta yccngayt                                                  198

<210> SEQ ID NO 4
<211> LENGTH: 198
<212> TYPE: DNA
<213> ORGANISM: Artificial Sequence
<220> FEATURE:
<223> OTHER INFORMATION: nonsense oligonucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)

```
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
```

<222> LOCATION: (119)..(119)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 4 gncgraaanac ncgrtcngar ttraanggrc arttrcanac nggratngar tgnagncgnc     60 gnagraaanac ngcnagngcr tcnacratrt tytcnccnga rtcnggrtay tcytcnagna    120
cytgraangc ngtyttnccn ggratngcng tngtnagnag ccangcrtcr tcnggngtnc    180
gratraartg yttratng                                                   198

<210> SEQ ID NO 5
<211> LENGTH: 198
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (2)..(2)

```
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
```

```
<222> LOCATION: (104)..(104)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 5
cnggngaraa yatygtngay gcnctngcng tnttyctncg ncgnctncay tcnatyccng     60
tntgyaaytg yccnttyaay tcngaycgng tnttycgnct ngcncargcn cartcncgna    120
tgaayaaygg nctngtngay gcntcngayt tygaygayga rcgnaayggn tggccngtng    180
arcargtntg gaargara                                                 198

<210> SEQ ID NO 6
<211> LENGTH: 198
<212> TYPE: DNA
<213> ORGANISM: Artificial Sequence
<220> FEATURE:
<223> OTHER INFORMATION: nonsense oligonucleotide
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (11)..(11)
```

-continued

```
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
```

```
<222> LOCATION: (161)..(161)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 6
trcanccrat nagyttnccy tcrtcraara tnagrttrtc nagngaraar tcnccrtgng      60
tnacnacnga rttraarcar aanggnagna gyttrtgcat ytcyttccan acytgytcna     120
cnggccancc rttncgytcr tcrtcraart cngangcrtc nacnagnccr ttrttcatnc     180
gngaytgngc ytgngcna                                                    198

<210> SEQ ID NO 7
<211> LENGTH: 198
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
```

```
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
```

<222> LOCATION: (179)..(179)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 7
tgcayaarct nctnccntty tgyttyaayt cngtngtnac ncayggngay ttytcnctng    60
ayaayctnat yttygaygar ggnaarctna tyggntgyat ygaygtnggn cgngtnggna   120
tygcngaycg ntaycargay ctngcnatyc tntggaaytg yctnggngar ttytcnccnt   180
cnctncaraa rcgnctnt                                                 198

<210> SEQ ID NO 8
<211> LENGTH: 173
<212> TYPE: DNA
<213> ORGANISM: Artificial Sequence
<220> FEATURE:
<223> OTHER INFORMATION: nonsense oligonucleotide
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (97)..(97)

```
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t

<400> SEQUENCE: 8
tcaraaraay tcrtcnagca tnagrtgraa ytgnagyttr ttcatrtcng grttrtcrat      60
nccrtaytty tgraanagnc gyttytgnag nganggngar aaytcnccna grcarttcca    120
nagratngcn agrtcytgrt ancgrtcngc ratnccnacn cgnccnacrt cra           173

<210> SEQ ID NO 9
<211> LENGTH: 125
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
```

```
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (75)..(78)
<223> OTHER INFORMATION: n is a, c, g, or t
<220> FEATURE:
<221> NAME/KEY: misc_feature
<222> LOCATION: (80)..(83)
<223> OTHER INFORMATION: n is a, c, g, or t
<220> FEATURE:
<221> NAME/KEY: misc_feature
<222> LOCATION: (85)..(88)
<223> OTHER INFORMATION: n is a, c, g, or t
<220> FEATURE:
<221> NAME/KEY: misc_feature
<222> LOCATION: (90)..(93)
<223> OTHER INFORMATION: n is a, c, g, or t
<220> FEATURE:
<221> NAME/KEY: misc_feature
<222> LOCATION: (95)..(98)
<223> OTHER INFORMATION: n is a, c, g, or t

<400> SEQUENCE: 9
tycaraarta yggnatygay aayccngaya tgaayaarct ncarttycay ctnatgctng      60
aygarttytt ytgannnnan nnntnnnncn nnnannnnta agcttgagtc agtttcagct     120
acctg                                                                125

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
atatcgcgga cacgtacctc gcaga                                           25

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
aatcttcgac ggtggaccgt tgttg                                           25

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
atggcgtaaa ggcatgtcac tttca                                           25

<210> SEQ ID NO 13
<211> LENGTH: 25
<212> TYPE: DNA
<213> ORGANISM: Artificial Sequence
<220> FEATURE:
<223> OTHER INFORMATION: primer
```

```
<400> SEQUENCE: 13
acgcctacct gctccagcta tcggc                                           25

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
attccactta tgtgtataac cacaa                                           25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
atcactctac ggtcgagagc tcgca                                           25

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
attgcctgta gtgttattac ttaga                                           25

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
ataactcaga ggagaatctg tacga                                           25

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
atttcggtca gatttatccc actaa                                           25

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
aatccttgga gtcccaccca ttgct                                           25

<210> SEQ ID NO 20
<211> LENGTH: 25
```

```
<212> TYPE: DNA
<213> ORGANISM: Artificial Sequence
<220> FEATURE:
<223> OTHER INFORMATION: primer

<400> SEQUENCE: 20
caaacagcaa atgttcttcc tgaaa                                          25

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
aaaactgcac gacgcaccag tttag                                          25

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
caatcagata gagatcttac atgaa                                          25

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
atcgatatct gcaacaaaca tttag                                          25

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
cacgctccta taacttcatc tagta                                          25

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
acccgttcta gccggattct taaat                                          25

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
```
cagactctta tctctttaac cgcta                                25

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
acatctgtag ggataatcgg tcccc                                25

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
catcctaaca ggggttctcc gttaa                                25

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
aagcgtccac gtaagagact tggtc                                25

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
cccacattta cagcttcttc ggtta                                25

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
atgcttaacg gggttataaa tttca                                25

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
ctgcctatga ctggtgtccc tgata                                25

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
atactttatc gctagaccaa ttaac                                                25

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
gaatcttaga aaattgatac gatga                                                25

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
ataaattact gaaagaactc tctta                                                25

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
gaatcttgaa atcatttaac aatga                                                25

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
acgcattgcc gccacaagga ttcgt                                                25

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
gacgcattga ctactttgtc ttgga                                                25

<210> SEQ ID NO 39
<211> LENGTH: 25
<212> TYPE: DNA
<213> ORGANISM: Artificial Sequence
<220> FEATURE:
<223> OTHER INFORMATION: primer

<400> SEQUENCE: 39
accgctttga gttctatttt tggca                                                25

```
<210> SEQ ID NO 40
<211> LENGTH: 25
<212> TYPE: DNA
<213> ORGANISM: Artificial Sequence
<220> FEATURE:
<223> OTHER INFORMATION: primer

<400> SEQUENCE: 40
aatactttaa ttcttatgtc tatta                                    25

<210> SEQ ID NO 41
<211> LENGTH: 25
<212> TYPE: DNA
<213> ORGANISM: Artificial Sequence
<220> FEATURE:
<223> OTHER INFORMATION: primer

<400> SEQUENCE: 41
atacatcttg gtcctagtca tcatg                                    25

<210> SEQ ID NO 42
<211> LENGTH: 25
<212> TYPE: DNA
<213> ORGANISM: Artificial Sequence
<220> FEATURE:
<223> OTHER INFORMATION: primer

<400> SEQUENCE: 42
aattccacaa atagttaatc gatta                                    25

<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
attgttcgat ggcataaagg tgcct                                    25

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
aattcctgaa gtgtttcagc tttaa                                    25

<210> SEQ ID NO 45
<211> LENGTH: 25
<212> TYPE: DNA
<213> ORGANISM: Artificial Sequence
<220> FEATURE:
<223> OTHER INFORMATION: primer

<400> SEQUENCE: 45
actaatcgca gatggatgtc tcaac                                    25

<210> SEQ ID NO 46
<211> LENGTH: 25
<212> TYPE: DNA
<213> ORGANISM: Artificial Sequence
<220> FEATURE:
<223> OTHER INFORMATION: primer
```

<400> SEQUENCE: 46
aattcgttaa catataagtc tttga                                    25

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
acacgtcaac gtcatacgcc tactc                                    25

<210> SEQ ID NO 48
<211> LENGTH: 25
<212> TYPE: DNA
<213> ORGANISM: Artificial Sequence
<220> FEATURE:
<223> OTHER INFORMATION: primer

<400> SEQUENCE: 48
agatcgccaa ttgatctttc tagga                                    25

<210> SEQ ID NO 49
<211> LENGTH: 25
<212> TYPE: DNA
<213> ORGANISM: Artificial Sequence
<220> FEATURE:
<223> OTHER INFORMATION: primer

<400> SEQUENCE: 49
atgactacca ggtctatccc tcaga                                    25

<210> SEQ ID NO 50
<211> LENGTH: 25
<212> TYPE: DNA
<213> ORGANISM: Artificial Sequence
<220> FEATURE:
<223> OTHER INFORMATION: primer

<400> SEQUENCE: 50
aggacaacca cttttcaagc agcaa                                    25

<210> SEQ ID NO 51
<211> LENGTH: 25
<212> TYPE: DNA
<213> ORGANISM: Artificial Sequence
<220> FEATURE:
<223> OTHER INFORMATION: primer

<400> SEQUENCE: 51
accgatgtac ggcccacgtc tcgct                                    25

<210> SEQ ID NO 52
<211> LENGTH: 25
<212> TYPE: DNA
<213> ORGANISM: Artificial Sequence
<220> FEATURE:
<223> OTHER INFORMATION: primer

<400> SEQUENCE: 52
gactcttcta ggttttcttc tttca                                    25

<210> SEQ ID NO 53

```
<211> LENGTH: 25
<212> TYPE: DNA
<213> ORGANISM: Artificial Sequence
<220> FEATURE:
<223> OTHER INFORMATION: primer

<400> SEQUENCE: 53
aatcttgggc gcatgaccct tccgt                                           25

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
gatgctggga cacgttaccc ttaga                                           25

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55
agccattgtt gagctatgca tcacg                                           25

<210> SEQ ID NO 56
<211> LENGTH: 25
<212> TYPE: DNA
<213> ORGANISM: Artificial Sequence
<220> FEATURE:
<223> OTHER INFORMATION: primer

<400> SEQUENCE: 56
gccgcgtaaa aggcttatcc agaca                                           25

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
acccctggga gcgccaactc ttaac                                           25

<210> SEQ ID NO 58
<211> LENGTH: 25
<212> TYPE: DNA
<213> ORGANISM: Artificial Sequence
<220> FEATURE:
<223> OTHER INFORMATION: primer

<400> SEQUENCE: 58
ggagctgtta catttttaac ttcaa                                           25

<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59
```
acacgtaaca gttccacacc tggct                                          25

<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
ggagctgtta cattttaac ttcaa                                           25

<210> SEQ ID NO 61
<211> LENGTH: 25
<212> TYPE: DNA
<213> ORGANISM: Artificial Sequence
<220> FEATURE:
<223> OTHER INFORMATION: primer

<400> SEQUENCE: 61
aaaactcttt gcgccacaca tctcg                                          25

<210> SEQ ID NO 62
<211> LENGTH: 25
<212> TYPE: DNA
<213> ORGANISM: Artificial Sequence
<220> FEATURE:
<223> OTHER INFORMATION: primer

<400> SEQUENCE: 62
ggccccgtca agcatgcgtc ttata                                          25

<210> SEQ ID NO 63
<211> LENGTH: 25
<212> TYPE: DNA
<213> ORGANISM: Artificial Sequence
<220> FEATURE:
<223> OTHER INFORMATION: primer

<400> SEQUENCE: 63
agaagtaatt gctggacgtc tgcaa                                          25

<210> SEQ ID NO 64
<211> LENGTH: 25
<212> TYPE: DNA
<213> ORGANISM: Artificial Sequence
<220> FEATURE:
<223> OTHER INFORMATION: primer

<400> SEQUENCE: 64
ggctctagaa taatttgatc gataa                                          25

<210> SEQ ID NO 65
<211> LENGTH: 25
<212> TYPE: DNA
<213> ORGANISM: Artificial Sequence
<220> FEATURE:
<223> OTHER INFORMATION: primer

<400> SEQUENCE: 65
acccgtaatg ggctgaaacg tcgcg                                          25

<210> SEQ ID NO 66
<211> LENGTH: 102
<212> TYPE: DNA

```
<213> ORGANISM: Artificial Sequence
<220> FEATURE:
<223> OTHER INFORMATION: insert fragment
<220> FEATURE:
<221> NAME/KEY: misc_feature
<222> LOCATION: (11)..(30)
<223> OTHER INFORMATION: n is a, c, g, or t
<220> FEATURE:
<221> NAME/KEY: misc_feature
<222> LOCATION: (75)..(94)
<223> OTHER INFORMATION: n is a, c, g, or t

<400> SEQUENCE: 66
gaattccctg nnnnnnnnnn nnnnnnnnnn cagcagctga agagatctgg atccgcggcc      60
gccttcagct gctgnnnnnn nnnnnnnnnn nnnnttctgc ag                       102

<210> SEQ ID NO 67
<211> LENGTH: 87
<212> TYPE: DNA
<213> ORGANISM: Artificial Sequence
<220> FEATURE:
<223> OTHER INFORMATION: junk sequence

<400> SEQUENCE: 67
tacaaatccg cctagagcgg atttgaacgt tgctgaagca acggcccgga gggtggccag      60
gacggccatt gactgccagg aattaac                                         87

<210> SEQ ID NO 68
<211> LENGTH: 188
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
```

<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t

<400> SEQUENCE: 68

```
aaagaaatgc ataaactttt gccattctgy ctntcntayg aracngarat yctnacngtn    60
gartayggnc tnctnccnat yggnaaraty gtngaraarc gnatygartg yacngtntay   120
tcngtngaya ayaayggnaa yatytayacn carccngtng cncartggca ygaycgnggn   180 garcarga                                                           188
```

<210> SEQ ID NO 69
<211> LENGTH: 188
<212> TYPE: DNA
<213> ORGANISM: Artificial Sequence
<220> FEATURE:
<223> OTHER INFORMATION: nonsense oligonucleotide
<220> FEATURE:
<221> NAME/KEY: misc_feature
<222> LOCATION: (7)..(7)
<223> OTHER INFORMATION: n is a, c, g, or t
<220> FEATURE:

```
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
```

<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t

<400> SEQUENCE: 69
rtcratnggn agcatytgnc crtcnacngt catraayttr tgrtcyttng tngcncgrat    60
nagnganccr tcytcnagrc artaytcraa nacytcytgy tcncncgrt crtgccaytg   120 ngcnacnggy tgngtrtara trttnccrtt rttrtcnacn gartanacng trcaytcrat  180 ncgyttyt                                                          188

<210> SEQ ID NO 70
<211> LENGTH: 188
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:

<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 70
rgtnttygar taytgyctng argayggntc nctnatycgn gcnacnaarg aycayaartt      60
yatgacngtn gayggncara tgctnccnat ygaygaraty ttygarcgng arctngayct     120
natgcgngtn gayaayctnc cnaayatyaa ratygcnacn cgnaartayc tnggnaarca     180 raaygtnt                                                              188

<210> SEQ ID NO 71
<211> LENGTH: 188
<212> TYPE: DNA
<213> ORGANISM: Artificial Sequence
<220> FEATURE:
<223> OTHER INFORMATION: nonsense oligonucleotide
<220> FEATURE:
<221> NAME/KEY: misc_feature

```
<222> LOCATION: (24)..(29)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
```

<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t

<400> SEQUENCE: 71

```
aaatcaccat gggtgactac tgannnnnng carttngang cratraancc rttyttnagn      60
gcraarttrt grtcncgytc nacnccratr tcrtanacrt tytgyttncc nagrtayttn     120
cgngtngcra tyttratrtt nggnagrttr tcnacncgca tnagrtcnag ytcncgytcr    180 aaratytc                                                             188
```

<210> SEQ ID NO 72
<211> LENGTH: 188
<212> TYPE: DNA
<213> ORGANISM: Artificial Sequence
<220> FEATURE:
<223> OTHER INFORMATION: sense oligonucleotide
<220> FEATURE:
<221> NAME/KEY: misc_feature
<222> LOCATION: (24)..(29)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature

```
<222> LOCATION: (123)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t

<400> SEQUENCE: 72
aaatcaccat gggtgactac tgannnnnnc garttngang cratraancc rttyttnagn      60
gcraarttrt grtcncgytc nacnccratr tcrtanacrt tytgyttncc nagrtayttn     120
cgngtngcra tyttratrtt nggnagrttr tcnacncgca tnagrtcnag ytcncgytcr     180 aaratytc                                                              188
```